United States Patent [19]
Schulman et al.

[11] Patent Number: 5,938,691
[45] Date of Patent: Aug. 17, 1999

[54] MULTICHANNEL IMPLANTABLE COCHLEAR STIMULATOR

[75] Inventors: Joseph H. Schulman, Santa Clarita; John C. Gord, Venice; Primoz Strojnik, Granada Hills; David I. Whitmoyer, Los Angeles; James H. Wolfe, Canyon Country, all of Calif.

[73] Assignee: Alfred E. Mann Foundation, Sylmar, Calif.

[21] Appl. No.: 09/103,264

[22] Filed: Jun. 23, 1998

Related U.S. Application Data

[62] Division of application No. 08/450,041, May 25, 1995, Pat. No. 5,776,172, which is a continuation of application No. 08/322,065, Oct. 12, 1994, Pat. No. 5,531,774, which is a continuation-in-part of application No. 08/023,584, Feb. 26, 1993, Pat. No. 5,603,726, which is a continuation of application No. 07/752,069, Aug. 29, 1991, abandoned, which is a continuation-in-part of application No. 07/411,563, Sep. 22, 1989, abandoned.

[51] Int. Cl.$^6$ .............................. A61N 1/36; A61F 2/18; H04R 25/00
[52] U.S. Cl. ................................................. 607/57; 607/55
[58] Field of Search .......................................... 607/55–57

[56] References Cited

U.S. PATENT DOCUMENTS

| | | |
|---|---|---|
| 4,532,930 | 8/1985 | Crosby et al. ............................. 607/57 |
| 4,592,359 | 6/1986 | Galbraith ................................. 607/57 |
| 4,947,844 | 8/1990 | McDermott .............................. 607/57 |

*Primary Examiner*—William E. Kamm
*Assistant Examiner*—Carl H. Layno
*Attorney, Agent, or Firm*—Alfred E. Mann Foundation

[57] ABSTRACT

A cochlea stimulation system includes a patient wearable system comprising an externally wearable signal processor (WP) and a headpiece in electronic communication with an implanted cochlear stimulator (ICS). The ICS comprises eight output stages each having two electrically isolated capacitor-coupled electrodes, designated "A" and "B", circuits for monitoring the voltages on these electrodes, and circuits for both transmitting status information to and receiving control information from the WP. Based upon information received from the WP, a processor within the ICS can control both the frequency and the widths of the output stimulation pulses applied to the electrodes and may select which electrodes to monitor. The ICS receives power and data signals telemetrically through the skin from the WP. To save power, the ICS may be "powered down" by the WP based upon the absence of audio information or "powered up" if audio is present. The WP communicates with the headpiece over a co-axial cable using one frequency for transmitting signals and a second different frequency for receiving signals.

15 Claims, 15 Drawing Sheets

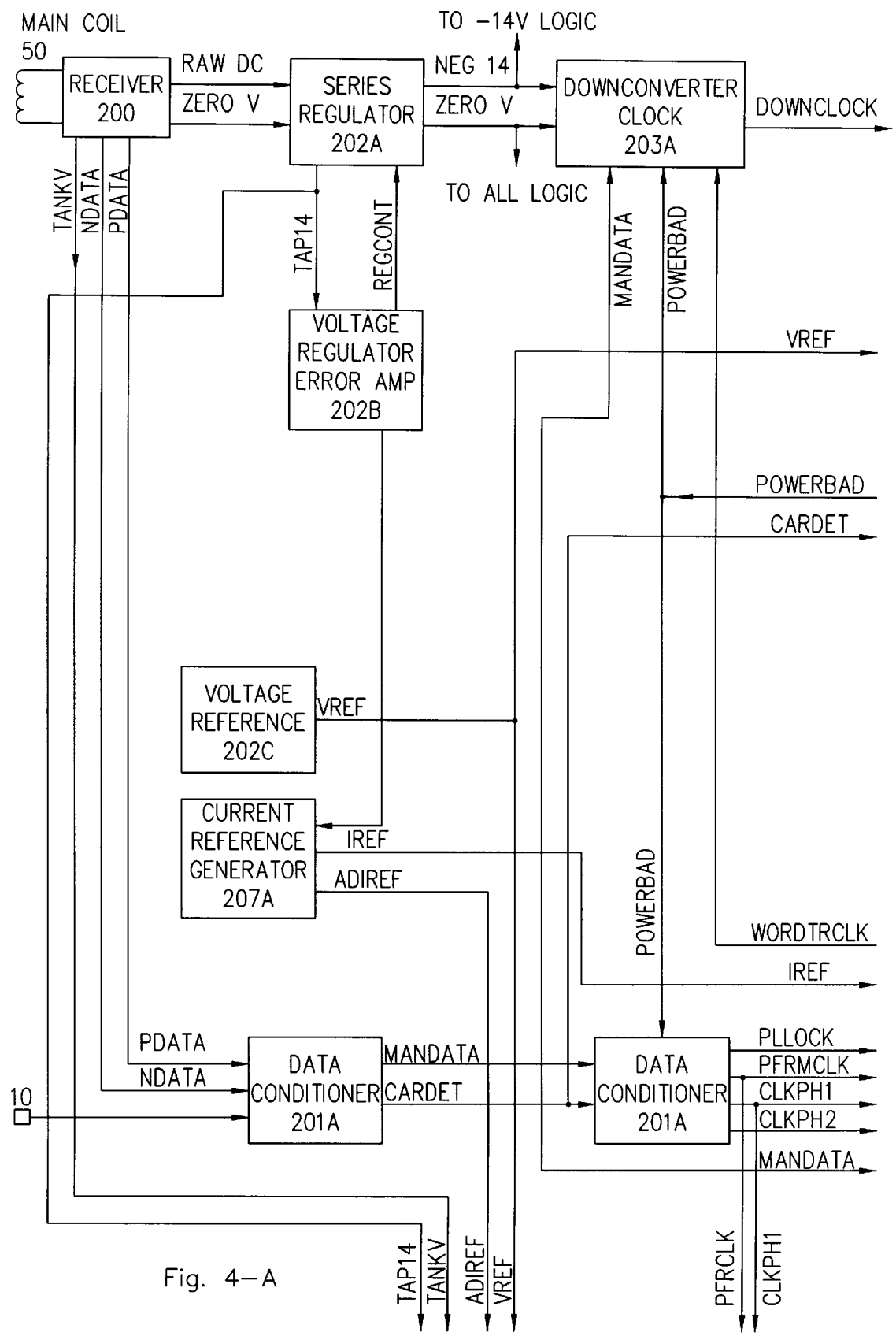
Fig. 4-A

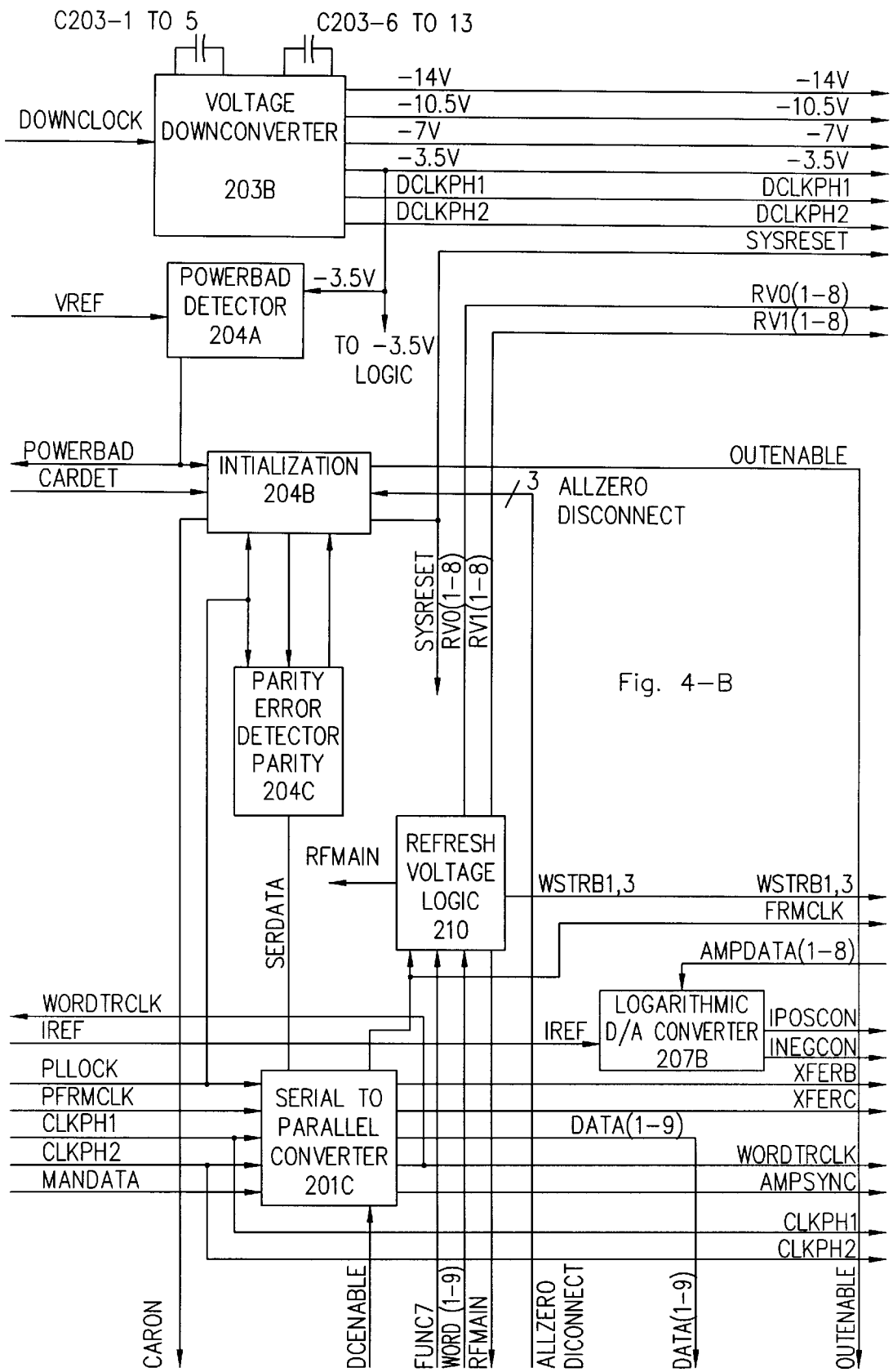
Fig. 4-B

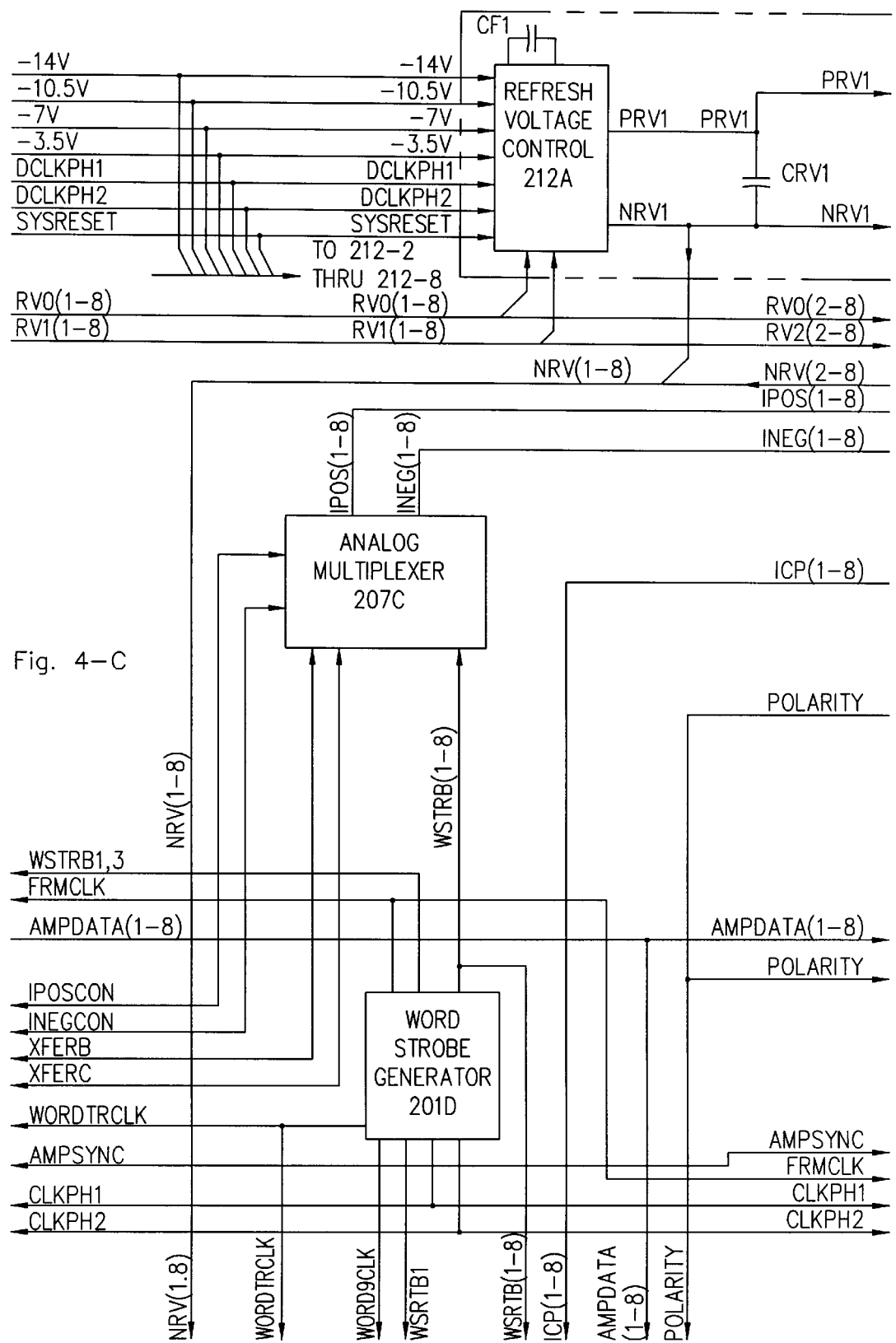
Fig. 4-C

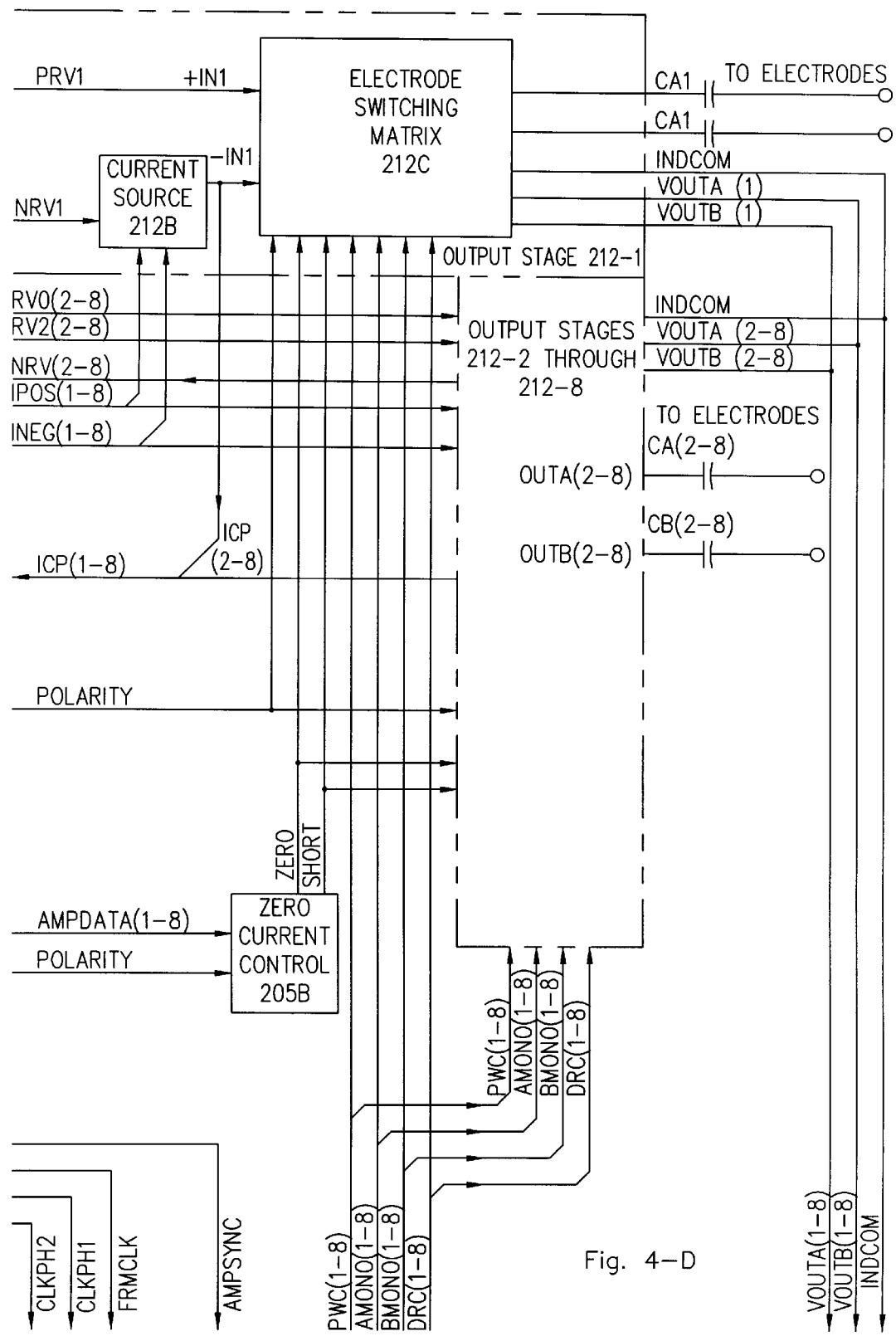
Fig. 4-D

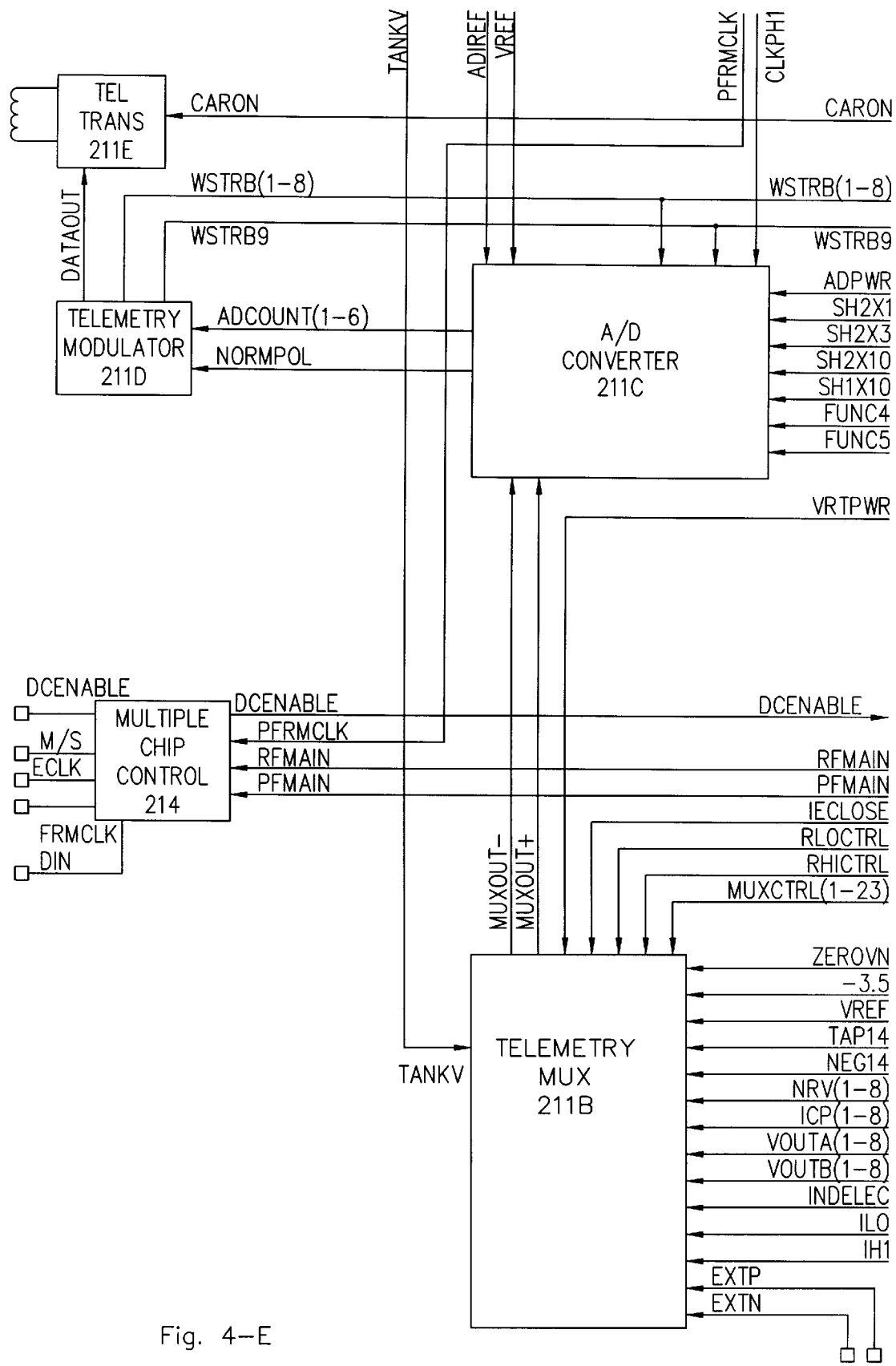
Fig. 4-E

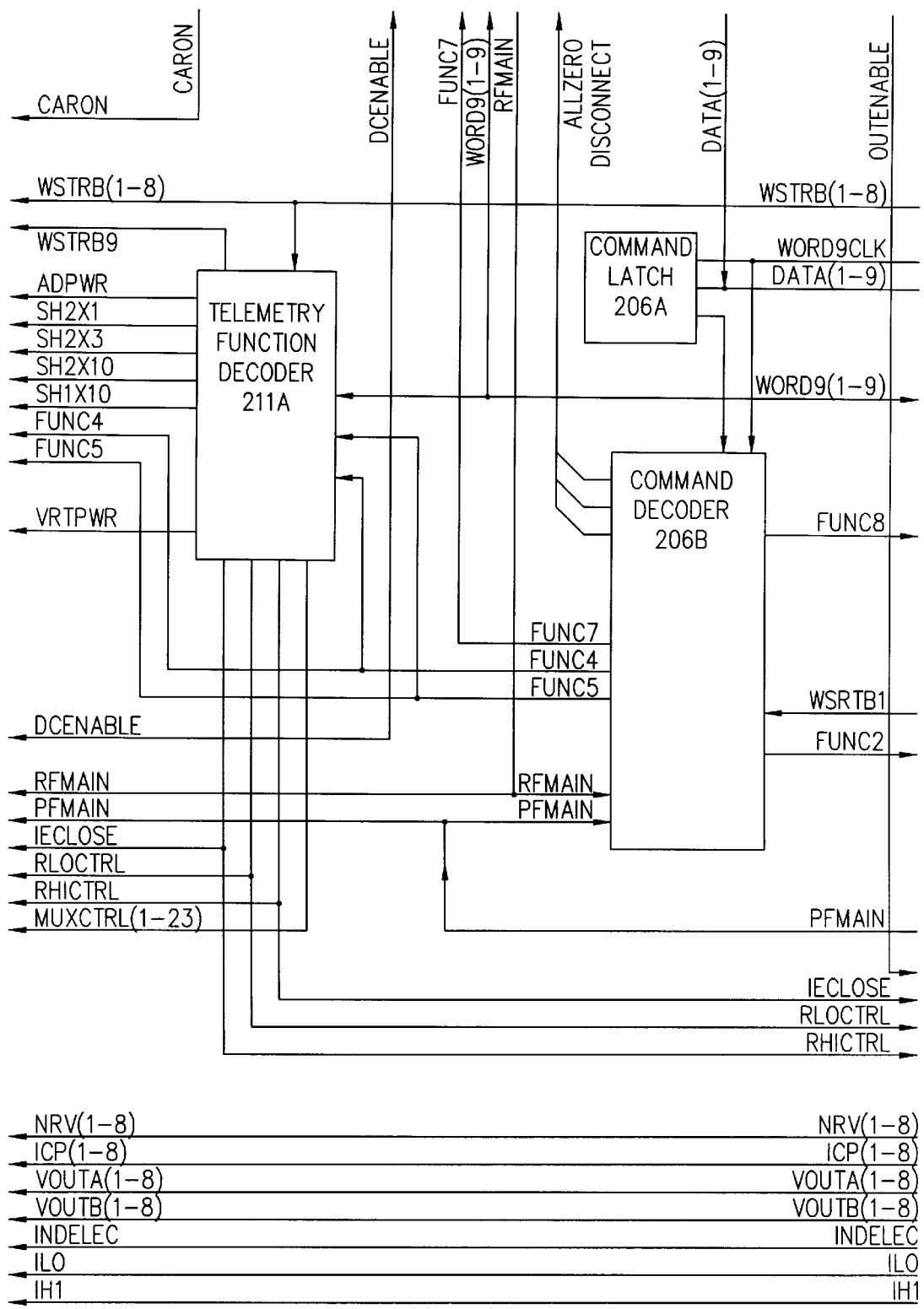
Fig. 4-F

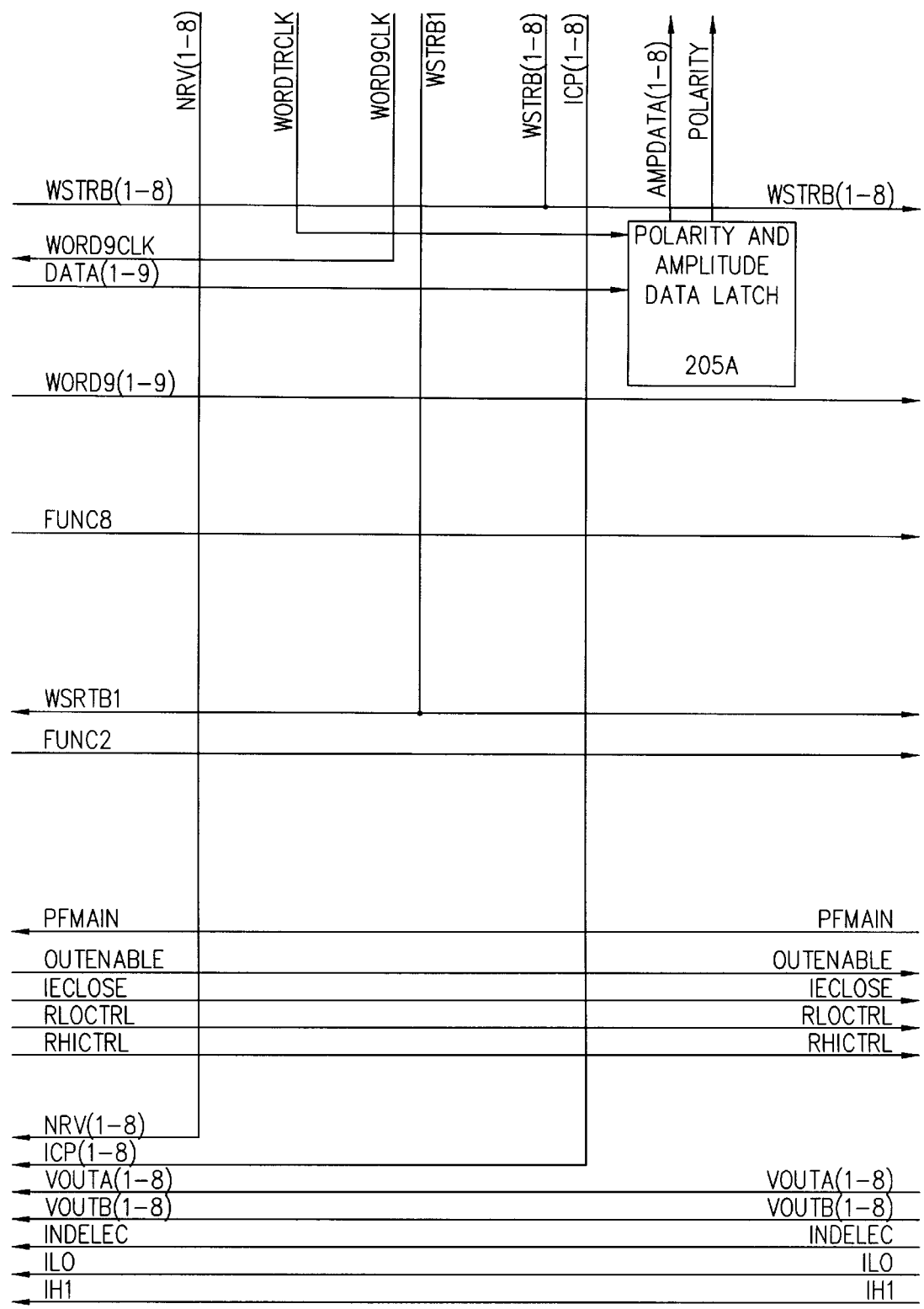
Fig. 4-G

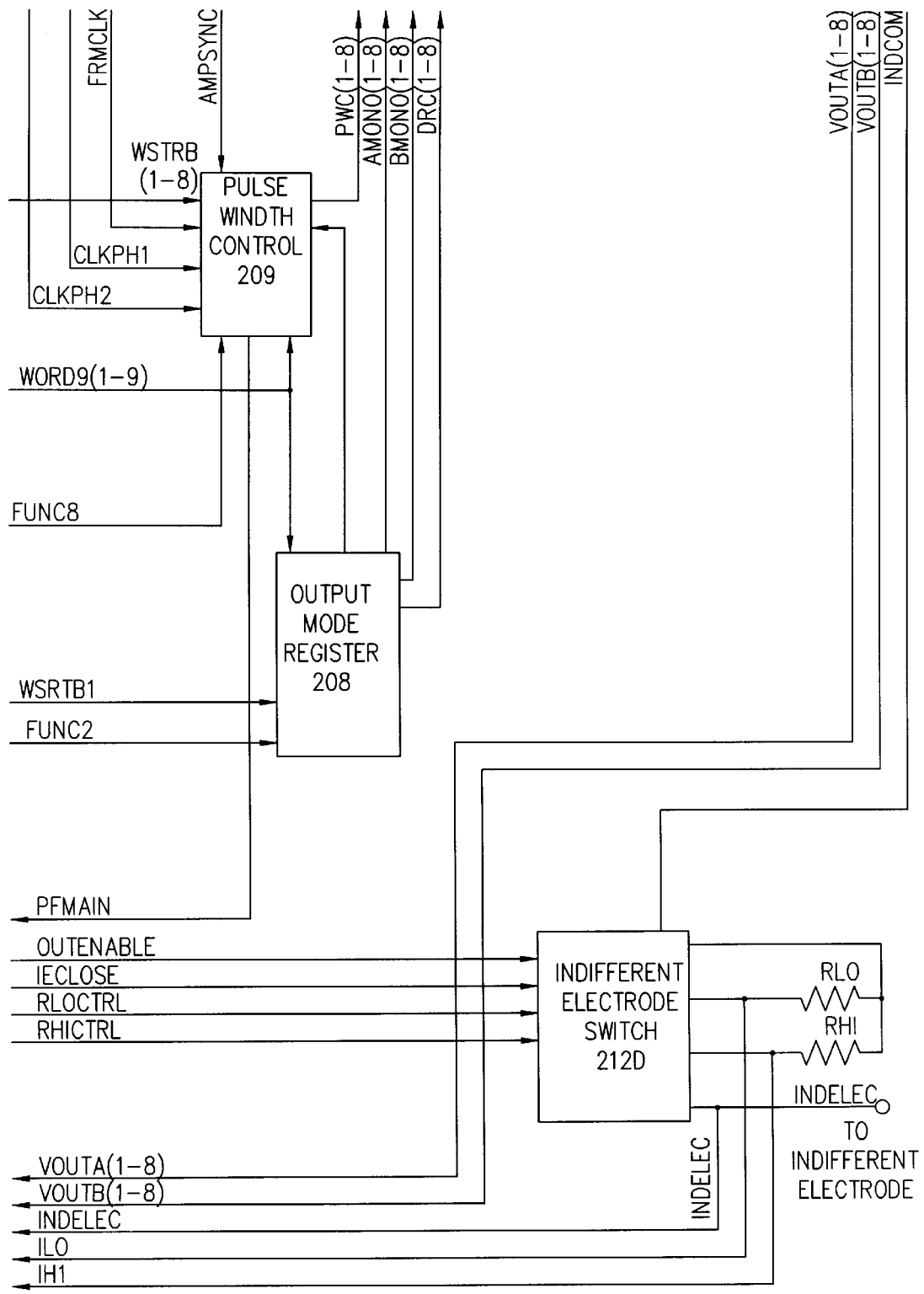
Fig. 4-H

LONG DATA FRAME FOR MULTIPLE CHIP OPERATION

PHYSICIAN'S TESTER

MULTICHANNEL IMPLANTABLE COCHLEAR STIMULATOR

RELATED APPLICATIONS

This application is a divisional application of application Ser. No. 08/450,041, filed May 25, 1995, now U.S. Pat. No. 5,776,172; which is a continuation of application Ser. No. 08/322,065, filed Oct. 12, 1994, now U.S. Pat. No. 5,531,774; which is a continuation-in-part of application Ser. 08/023,584, filed Feb. 26, 1993, now U.S. Pat. No. 5,603,726; which is a continuation of application Ser. No. 07/752,069, filed Aug. 29, 1991, now abandoned; which is a continuation-in-part of patent application Ser. No. 07/411,563, filed Sep. 22, 1989, also abandoned.

BACKGROUND

The present invention relates to improvements in human tissue stimulators and more particularly to a human tissue stimulating system which in a preferred form comprises an audio responsive system for artificially stimulating the cochlea to improve the hearing of the hearing impaired.

U.S. Pat. No. 4,400,590 issued Aug. 23, 1983 for "Apparatus for Multi-Channel Cochlear Implant Hearing Aid System" describes and illustrates a multi-channel intra-cochlear electrode and system for electrically stimulating predetermined locations of the auditory nerve within the cochlea of the ear. The electrode comprises a plurality of exposed electrode pairs spaced along and embedded in a resilient curved base for implantation in accordance with the method of surgical implantation described in U.S. Pat. No. 3,751,615 issued Aug. 7, 1973 for "Method of Inducing Hearing." The hearing aid system described in the '590 patent receives audio signals at a signal processor located outside the body of a hearing impaired patient. The processor converts the audio signals into analog data signals which are transmitted by a cable connection through the patient's skin to the implanted multi-channel intra-cochlear electrode. The analog signals are applied to selected ones of the plurality of exposed electrode pairs included in the intra-cochlear electrode to electrically stimulate predetermined locations of the auditory nerve within the cochlea of the ear where the intra-cochlear electrode is positioned.

The cochlea stimulating system described in the '590 patent is limited in the number of channels of information, the speed of transfer of stimulating signals to the cochlea and the fidelity of the signals. Also, the cable connection through the skin of the patient to the intra-cochlear electrode is undesired in that it interferes with the freedom of movement of the patient and represents a possible source of infection.

U.S. Pat. No. 4,532,930, issued Aug. 6, 1985 for "Cochlear Implant System For an Auditory Prosthesis" describes and illustrates a multiple electrode system. While multiple electrodes are employed to stimulate hearing the system only operates with a single pulsatile output stimulating a single electrode channel at any given time. Such a sequential system is limited in speed of operation and does not provide for analog operation where continuous stimulating signals controllable in amplitude are simultaneously applied to a number of electrode channels. Further, the system is subject to charge imbalance with misprogramming or circuit fault and inefficient use of electrical power. Moreover, once the stimulator unit is implanted there are no means for monitoring its ongoing circuit operation or power requirements so as to optimize its continued operation.

U.S. Pat. No. 4,592,359, issued Jun. 3, 1986 for "Multi-Channel Implantable Neural Stimulator" describes a cochlear implant system having 4 current sources and 4 current sinks per channel controlled by series switches to provide 16 different circuits for supplying 16 levels of 2 polarities to each output channel. In a pulsatile mode, the system provides for simultaneous update (amplitude control) and output to all channels. However, the system does not permit simultaneous analog update and output on all channels and the electrode pairs for each channel are not electrically isolated from all other electrode pairs whereby undesired current leakage may occur. Further, once the stimulator is implanted there are no means for monitoring its ongoing circuit operation or power requirements so as to optimize its continued operation.

U.S. Pat. No. 4,947,844, issued Aug. 14, 1990 for "Receiver/Stimulator For Hearing Prosthesis" describes and illustrates a multiple channel electrode system. The system includes an implanted receiver/stimulator connected to an implanted electrode array. The receiver/stimulator includes an electrode stimulating current control characterized in that current is delivered to each electrode or to each bipolar pair of electrodes in a series of short electrical pulses, each elemental pulse being separated from the next by an interval of zero current which has a longer duration than an elemental pulse. The waveform of the stimulus current comprises a series of pulses of one polarity followed by an equal number of pulses of an opposite polarity whereby the sum of all the electrical charge transferred through each electrode is approximately zero at the end of a stimulating current waveform. In this way, elemental current pulses applied to each electrode on each pair of electrodes which are stimulating are preferably delivered cyclically such that elemental pulses delivered to one electrode are interleaved in time with those delivered to any other electrodes. This enables the use of a single current source in the receiver/stimulator. The use of a single current source limits the operation of the receiver/stimulator in that the single current source must be switched to serve all output channels in a sequential manner. Simultaneous operation is not possible. Further, the number of channels cannot be greater than 3 or 4 without greatly reducing the duty cycle of the stimulating current waveform in each channel. Not only does the stimulus effectiveness in each channel suffer in such a situation, but the time required to complete the switching cycle for the single current source lengthens in direct proportion to the number of channels. Further, this system lacks output coupling capacitors in series with each electrode. This omission may lead to net DC current flow through the electrodes in the event of misprogramming or under circuit fault conditions.

The system described in the 844 patent also includes in the implanted receiver/stimulator a transmitter for telemetering one electrode voltage, measured during stimulation, to an external receiver for monitoring and analysis as an indicator of proper operation of the implanted stimulator. The transmitter comprises an oscillator operating at a frequency of about 1 MHz. The output of the oscillator is coupled to the implant's receiving coil and demodulated to recover the selected voltage waveforms. Unfortunately, such a telemetry system is not only limited to the monitoring of one voltage, but the simultaneous transmission of the telemetry signal and reception of the input carrier signal as described will result in undesired modulation and possible loss of input data.

Accordingly, there is a continuing need for an improved multi-channel tissue stimulator system particularly useful as a cochlear stimulator system and which is characterized (i) by a high operating speed in analog and pulsatile operation, (ii) freedom from charge imbalance, (iii) complete isolation of its electrode pairs for each channel, and (iv) the externally controllable monitoring and selective control a plurality of operating parameters and power supply to and currents and voltages developed within the implanted stimulator unit of the system to optimize system operation and power efficiency. The present invention satisfies such needs.

SUMMARY OF INVENTION

A preferred embodiment of the present invention comprises a cochlea stimulating system including an externally wearable signal receiver and processor (WP) and an implanted cochlea stimulator (ICS). The receiver, which may comprise a headpiece adjacent the ear of a patient, receives audio signals and transmits the audio signals to the WP. The WP receives and processes the audio signal and includes means for generating data indicative of the audio signals for transmission to the ICS.

The ICS includes means for receiving transmissions from the WP as well as a processor for processing such transmissions to sequentially update and simultaneously or sequentially generate and apply stimulation signals to a plurality of cochlea stimulating channels each having capacitor coupled electrodes implanted within the cochlea of the patient. The processor includes means responsive control signals from the WP for selectively monitoring one or more of the electrodes and voltages within the processor and for generating ICS status indicating signals. The ICS status indicating signals are telemetered back to the WP which includes means for receiving and processing the ICS status indicating signals. For example, such means may include means for controlling the power level of transmissions to the ICS.

The processor in the ICS also includes means for selectively controlling the pulse widths of the stimulation signals, the frequency at which stimulating signals are applied to selected electrodes, and means for generating a plurality of voltages for powering different components in the ICS and for selectively receiving and responding to analog and pulsatile input data signals from the WP.

Preferably, each channel in the ICS includes (i) a current source and floating current transfer device with switching capacitors for supplying stimulating signals to the capacitor coupled electrodes which are independent and isolated from the stimulating signals supplied to the output of all other channels, (ii) means for selectively driving the electrodes as unipolar or bipolar electrodes and (iii) means for powering down the ICS when audio signals are not received by the WP and for rapidly powering up the ICS in response to the reception of audio signals at the WP.

DETAILED DESCRIPTION OF INVENTION

The preferred forms of the present invention are implemented using CMOS technology. In development of the invention, however, a prototype was developed using standard, off-the-shelf electrical components which when connected functioned in accord with the general principles and features set forth in the preferred forms of the system, including CMOS integrated circuits and chips. Thus, in duplicating the systems hereinafter described, one may either utilize conventional off-the-shelf electrical components or develop the systems utilizing techniques well known in CMOS technology, whichever is desired.

Figure 1:
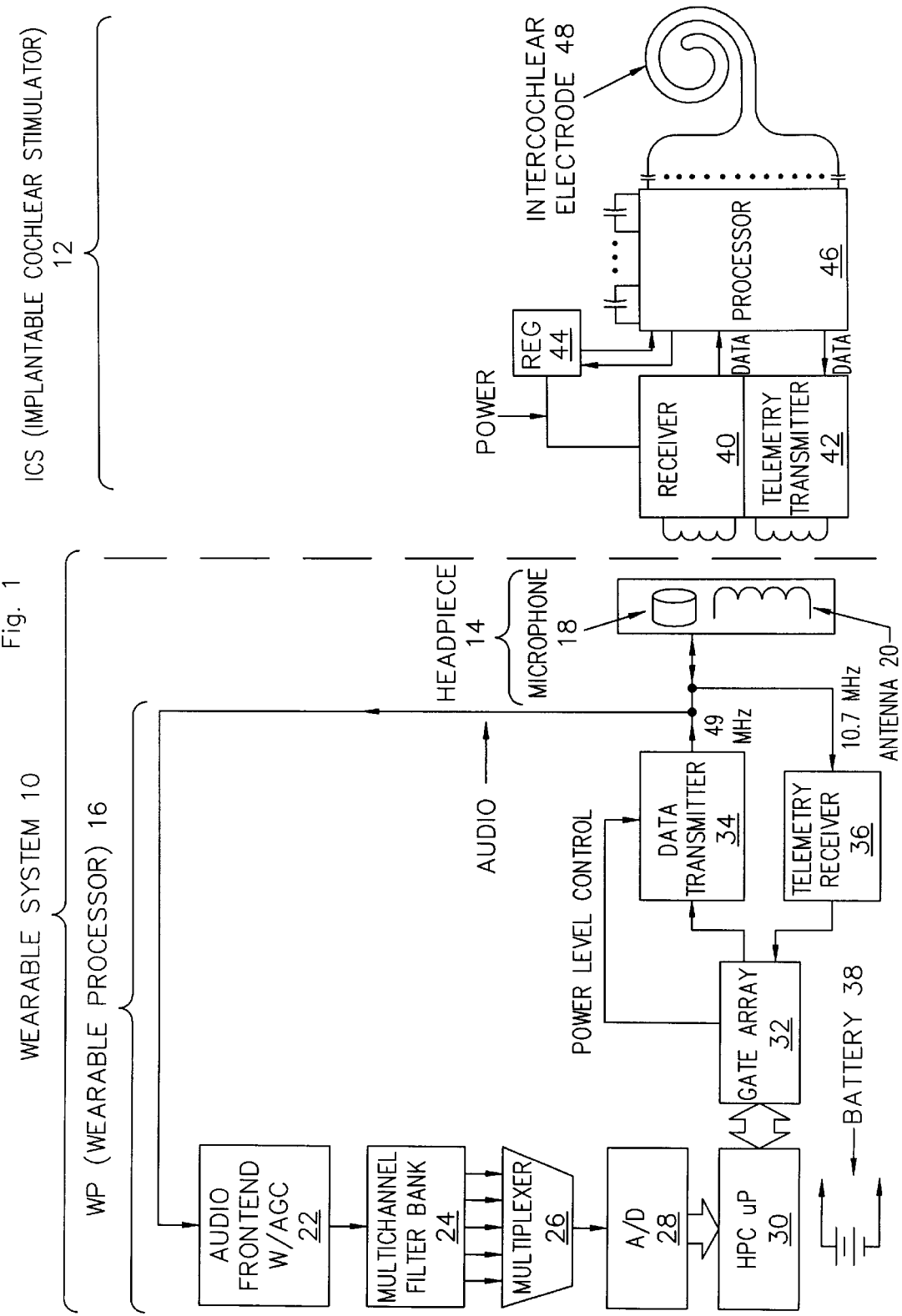
FIG. 1 is a block diagram of a basic form of a cochlea stimulating system comprising a preferred embodiment of the present invention.

As illustrated in FIG. 1, the basic system according to a preferred embodiment of the present invention basically comprises an externally wearable system 10 and an implantable cochlear stimulator (ICS) 12. The external system 10 comprises a headpiece 14 and an externally wearable processor (WP) 16. The headpiece may be worn behind the ear of a hearing impaired person and comprises a conventional microphone 18 and an antenna 20 for transmitting and receiving electromagnetic energy preferably in the form of radio frequency signals. Such coupling can be restricted to magnetic field only by an electrostatic shield around the coils comprising the antenna 20. In addition, signals from the ICS to the WP on one carrier frequency and from the WP to the ICS on another frequency can be transferred via a single coaxial cable between the headpiece 14 and the WP 16. This can be accomplished by having tuned inductor-capacitor filters for each frequency at each end of the coaxial cable.

The WP 16, powered by a battery 38, is adapted to receive audio signals received by the microphone 18 and to transmit such signals to a conventional audio front end 22 which features automatic gain control (AGC). The audio signals processed by the audio front end 22 are transmitted to a bank of filters 24 for filtering and for generation of a plurality of parallel audio signals. The audio signals are processed by a multiplexer 26 and converted to a series of digital signals by an A to D converter 28 for application to a microprocessor 30. The filter bank may also be implemented as a group of digital filters, for example in a digital signal processor integrated circuit. In this case the signal flow would be from the audio front end and AGC 22, through an anti-aliasing filter, to an analog to digital converter, then into a digital filter bank 24 and the general processing of microprocessor 30.

The output of the microprocessor 30 is coupled through a custom gate array 32 that converts data from the microprocessor into a serial bit stream going to a data transmitter 34. The gate array 32 also converts data from a telemetry receiver 36 and the microprocessor 30 to control the power level of and data generated by the data transmitter 34.

As illustrated in FIG. 1, the ICS 12 includes a receiver 40 for receiving data transmissions from the wearable system 10 and a telemetry transmitter 42 for transmitting ICS status indicating and measured signals from the ICS 12 to the wearable system 10 for processing thereby. For example, power level indicating signals transmitted by the telemetry transmitter 42 are received by the telemetry transmitter 36 and processed in the microprocessor 30 and gate array 32 to generate signals controlling the power level of the transmissions from the transmitter 34 to the ICS 12, thereby providing a closed-loop system for optimizing the power levels of the transmission from the wearable system 10 to the ICS 12 and hence conserving the battery 38 and optimizing the voltages generated within the system 10.

In addition to the receiver 40 and transmitter 42, the ICS 12 includes a regulator 44 for receiving a power signal from the receiver 40 to energize a processor 46. Data signals from the receiver 40 are also transmitted to the processor 46 for processing to generate stimulation signals applied to one or more of a plurality of capacitor coupled electrodes in an intra-cochlear electrode 48.

Generally speaking, in response to control or data signals from the WP16 the processor 46 selectively monitors voltages of the electrodes and associated circuitry in the processor and generates ICS status indicating and measured signals. For example, the processor 46 monitors the voltage applied to the regulator 44, the impedance of the electrodes and other voltages within the processor to generate the status indicating signals which are sent as data to the telemetry transmitter 42 for transmission to the wearable system 10.

More particularly, in the cochlea stimulating system shown in FIG. 1, the signals transmitted to the ICS 12 from the wearable system 10 include electrical power components. Such power components are processed within the receiver 40 through the series regulator 44 to generate a voltage signal which powers the processor 46. The processor 46 selectively monitors the voltage applied to the series regulator and generates a status indicating signal relative to such voltage which is transmitted by the telemetry transmitter 42 and received by the telemetry receiver 36. As previously stated, such information is utilized in the microprocessor 30 and gate array 32 of the WP 16 to control the power level of the transmissions from the data transmitter 34 to the ICS 12.

Figure 2:
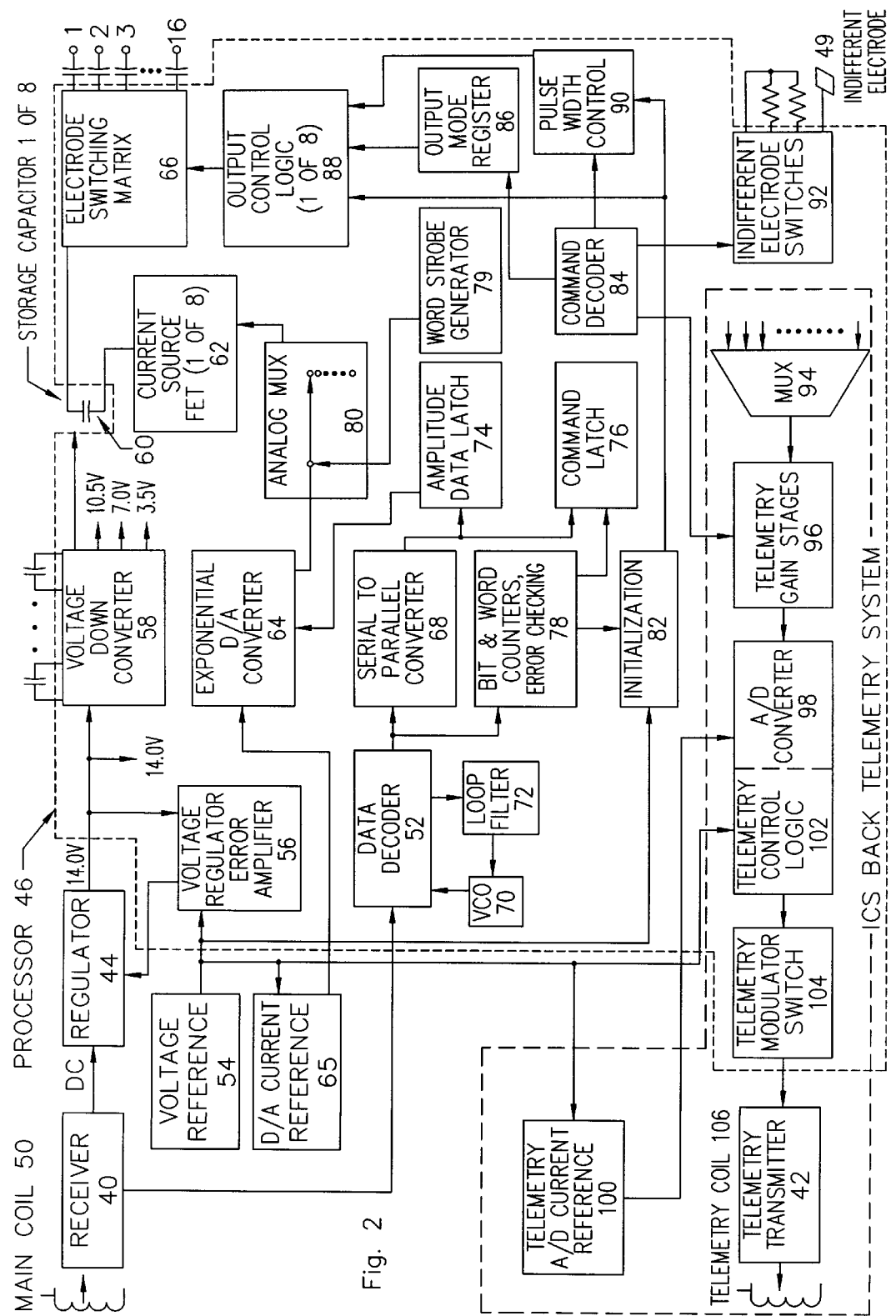
FIG. 2 is a more detailed block diagram of the ICS of FIG. 1 and associated circuitry for receiving and transmitting signals from and to the WP.

More specifically as to the ICS 12 and the embodiment thereof illustrated in FIG. 2, power and data are sent through a main coil 50 to the receiver 40 comprising a power rectifier which filters out DC power for the regulator 44 and a detector which demodulates the data for transmission to a data decoder 52. The regulator 44 in conjunction with a voltage reference 54 and voltage regulator error amplifier 56 produces a precise 14 volts for powering the balance of the processor 46. More particularly, the 14 volts powers a voltage downconverter 58 which generates three additional voltages, 10.5, 7.0 and 3.5 volts. The three voltages are used to power various other circuits, including the output circuits of the processor 46.

The voltage used to provide charge to the outputs applied to the electrodes 48 is transferred to eight different storage capacitors 60, one of which is illustrated in FIG. 2. There is one storage capacitor for each of eight isolated bipolar channels. The output of each storage capacitor is controlled by a current source FET 62 for that channel. Each FET current is determined by an exponential D to A converter 64 and current reference 65, such as the D to A converter described in U.S. Pat. No. 4,931,795 issued Jun. 5, 1990 and assigned to the same assignee as the present invention.

The output of the current sources 62 are connected to the electrodes 48 and an indifferent electrode 49 through a switch matrix 66. The output of the electrode switch matrix 66 is capacitor coupled to each of 16 electrodes. The following table lists the output currents available to the electrodes:

| Constant Current Amplitude Steps ($\mu A$) | | | | |
|---|---|---|---|---|
| 2500 | 470.6 | 88.58 | 16.67 | 3.138 |
| 2417 | 455.1 | 85.67 | 16.12 | 3.035 |
| 2338 | 440.1 | 82.86 | 15.59 | 2.936 |
| 2261 | 425.7 | 80.13 | 15.08 | 2.839 |
| 2187 | 411.7 | 77.50 | 14.58 | 2.746 |
| 2115 | 398.2 | 74.96 | 14.11 | 2.656 |
| 2046 | 385.1 | 72.49 | 13.64 | 2.568 |
| 1978 | 372.4 | 70.11 | 13.19 | 2.484 |
| 1913 | 360.2 | 67.81 | 12.76 | 2.402 |
| 1850 | 348.4 | 65.58 | 12.34 | 2.324 |
| 1790 | 336.9 | 63.43 | 11.94 | 2.247 |
| 1731 | 325.9 | 61.34 | 11.54 | 2.173 |
| 1674 | 315.2 | 59.33 | 11.16 | 2.102 |
| 1619 | 304.8 | 57.38 | 10.80 | 2.033 |
| 1566 | 294.8 | 55.49 | 10.44 | 1.966 |
| 1514 | 285.1 | 53.67 | 10.10 | 1.901 |
| 1465 | 275.7 | 51.91 | 9.772 | 1.839 |
| 1416 | 266.7 | 50.20 | 9.451 | 1.779 |
| 1370 | 257.9 | 48.55 | 9.140 | 1.720 |
| 1325 | 249.4 | 46.96 | 8.840 | 1.664 |
| 1281 | 241.2 | 45.42 | 8.549 | 1.609 |
| 1239 | 233.3 | 43.92 | 8.269 | 1.556 |
| 1198 | 225.6 | 42.48 | 7.997 | 1.505 |
| 1159 | 218.2 | 41.08 | 7.734 | 1.455 |
| 1121 | 211.1 | 39.73 | 7.480 | 1.408 |
| 1084 | 204.1 | 38.43 | 7.234 | 1.361 |
| 1049 | 197.4 | 37.17 | 6.997 | 1.317 |
| 1014 | 190.9 | 35.95 | 6.767 | 1.273 |
| 981.2 | 184.7 | 34.76 | 6.545 | 1.232 |
| 949.0 | 178.6 | 33.62 | 6.330 | 1.191 |
| 917.8 | 172.7 | 32.52 | 6.122 | 1.152 |
| 887.6 | 167.1 | 31.45 | 5.921 | 1.114 |
| 858.5 | 161.6 | 30.42 | 5.726 | 1.077 |
| 830.3 | 156.3 | 29.42 | 5.538 | 1.042 |
| 803.0 | 151.1 | 28.45 | 5.356 | 1.008 |
| 776.6 | 146.2 | 27.52 | 5.180 | 0.975 |
| 751.1 | 141.3 | 26.61 | 5.010 | 0.000 |
| 726.4 | 136.7 | 25.74 | 4.845 | |
| 702.6 | 132.2 | 24.89 | 4.686 | |
| 679.5 | 127.9 | 24.07 | 4.532 | |
| 657.2 | 123.7 | 23.28 | 4.383 | |
| 635.6 | 119.6 | 22.52 | 4.239 | |
| 614.7 | 115.7 | 21.78 | 4.100 | |
| 594.5. | 111.9 | 21.06 | 3.965 | |
| 575.0 | 108.2 | 20.37 | 3.835 | |
| 556.1 | 104.6 | 19.70 | 3.709 | |
| 537.8 | 101.2 | 19.05 | 3.587 | |
| 520.2 | 97.92 | 18.43 | 3.469 | |
| 503.1 | 94.70 | 17.82 | 3.355 | |
| 486.5 | 91.59 | 17.24 | 3.245 | |

Under control of a voltage controlled oscillator 70 and its loop filter 72, the serial output from the data decoder 52 drives a serial to parallel converter 68. The parallel output of the serial-to-parallel converter 68 provides channel amplitude data to an amplitude data latch 74 and program command data to a command latch 76. More particularly, the serial data from the data decoder 52 is analyzed by bit and word error checking counters 78. The amplitude data from the amplitude data latch 74 determines the output of the exponential D to A converter 64. In that regard, the analog value of the output from the D to A converter 64 is generated in a current mirror which is then transferred via an analog multiplexer 80 to the capacitively-coupled output electrodes 48. The sequence of operation of the multiplexer 80 is controlled by the output of a word strobe generator 79 which is driven by command latch 76. It should be noted that the command latch 76 cannot function unless an initialization circuit 82 and the bit error checking circuit 78 permit data to be transferred to a command decoder 84.

The command decoder 84 controls all the other specific functions such as the electrode switching matrix 66 via an output mode register 86 and output control logic 88, and a pulse width control 90 which also controls the output via the output control logic 88. As with the command latch, the pulse width control 90 and the output control logic 88 cannot function unless the initialization circuit 82 is properly initialized. To be enabled, the initialization circuit 82 must detect the correct initial digital code. When the initialization circuit 82 is not enabled, the electrode switching matrix 66 cannot turn on.

In addition to the other functions of the command decoder 84, it also controls the setting of indifferent electrode switches 92 which are used for monitoring the current flowing through the indifferent electrode and therefore through any or all 16 electrodes in a unipolar configuration. With the appropriate output channel configuration in the unipolar state, the indifferent electrode switches permit multi-polar operation.

As illustrated more clearly in FIG. 2, the ICS back telemetry system described briefly relative to FIG. 1, consists of a signal multiplexer (MUX) 94 programmed by the command decoder 84 to monitor various voltages throughout the processor 46 and ICS 12. The output of the multiplexer 94 is amplified through a series of telemetry gain stages 96 which are connected to an A to D converter 98. Power to the gain stages 96 can be turned on and off by the command decoder 84 to conserve energy when not in use.

The A to D converter 98 may be a single-slope type which functions by comparing the output of the gain stages 96 with a voltage ramp. The slope of the ramp is set by a current reference 100. The output of the A to D converter 98 and a telemetry control logic 102 is a train of bits that controls a telemetry modulator switch 104. The telemetry modulator switch 104 modulates the telemetry transmitter 42 which energizes a telemetry coil 106.

As previously indicated, the back telemetry system included in the cochlear stimulating system of the present invention provides means for minimizing power consumption of the system. As previously noted, the WP 16 is powered by the battery 38. To increase the battery life or to allow a smaller battery to be used, the radio frequency transmitted from the WP 16 via the antenna 20 to the ICS 12 is rectified in the receiver 40 and applied to the regulator 44. It is important that the output voltage of the regulator 44 be held constant, in this case, 14 volts. It is also important that the voltage regulator which has the 14 volt output must have somewhat more than 14 volts available as an input. Any additional voltage is lost as heat and will reduce the life of battery 38. In the present invention, the regulator input voltage (DC) is optimized by controlling the RF power transmitted by the wearable system 10 and received by the ICS 12. As previously indicated, the data transmitter 34 is powered by the battery 38, preferably a 6 volt 0.5 amp-hour battery. The power control is affected through a conventional switching regulator included in the gate array 32 whose output voltage may be varied based upon the duty cycle of a switching transistor or multiple switching transistors in the switching regulator. The output of the power control circuit powers the transmitter 34 and by varying its output voltage can vary the transmitter power. The transmitter may run at 49 MHz and be 100% amplitude modulated by a digital signal. The digital signal comes from the gate array 32. The signals transmitted by the transmitter 34 are received at the ICS 12 and rectified as previously described. The rectified power noted as "DC" in FIG. 2 is applied to the regulator 44 which may be of conventional design including a junction type depletion-mode FET to hold the output voltage of the regulator 44 constant as the input voltage changes. In practice, the input voltage can vary from 14 volts up to 20 volts or more. To maintain best efficiency, it is desired that the DC voltage be only slightly greater than the output voltage of the series regulator 44, perhaps on the order of 14.2 to 15 volts. However, as the antenna 20 is moved or as the circuit loads change, the DC voltage may start to change. One purpose of the back telemetry system is to allow the DC voltage to be automatically maintained at the lowest voltage consistent with normal operation. To accomplish this, under control of the command decoder 84, the multiplexer 94 monitors the DC voltage. The desired output of the multiplexer 94 is applied to the conventional A to D converter 98. As previously described, the output of the A to D converter, telemetry control logic 102 and telemetry modulator switch 104, FM modulates the telemetry transmitter 42 which may comprise a 10.7 MHz oscillator. The output of the oscillator is coupled back through the skin to the headpiece 14 and antenna 20 to the telemetry receiver 36. The output of the receiver 36 is applied to the gate array 32 including a conventional serial to parallel converter. The parallel data output from the serial to parallel converter is processed in the microprocessor 30 to adjust the power level in the power control circuit of the data transmitter 34 to maintain the value of the DC voltage slightly greater than the desired output voltage of the series regulator 44.

As just described, the command decoder 84 controls the monitoring of the value of the DC voltage to provide the desired voltage control. Similarly, the command decoder 84 may select particular channels to be monitored and the impedance of the various electrodes to be determined in the same manner as the DC voltage was monitored and as above described. In such cases, the ICS status indicating signals generated in the processor 46 and telemetered to the WP 16 may be utilized within the microprocessor 30 to provide indications of the operating status of the ICS 12.

In still other instances, to save power the command decoder 84 may function to cause a powering down of various subsystems within the processor 46. With the circuitry of FIG. 2, power may be restored in approximately 20 msec. on appropriate output from the command decoder. Similarly, the microprocessor can go into a hibernation state which consumes less than 10 milliwatts. The hibernation state terminates whenever additional commands are received from the command decoder 84.

In the ICS 12 illustrated in FIG. 2, the current sources 62 are floating. Such "floating" of the current sources may be as described in U.S. patent application Ser. No. 428,179, filed Dec. 18, 1989, and assigned to the same assignee as the present invention, and may be implemented with an FET that is not directly tied to a power supply. This may be implemented using two identically sized transistors, one being a reference transistor upon which an input current is impressed to generate a voltage difference thereacross which is a predetermined gate voltage for the second or output transistor which is floating with respect to all power supplies. The predetermined gate voltage is that voltage which when applied to the output transistor will produce the same current value as the input current. The importance of such floating current sources in the ICS 12 is to enable the ICS 12 to stimulate pairs of electrodes independent of the current flow in other pairs of electrodes and independent from the main power supply. This allows for the exact control of current in each output stage with no direct current path back to the main power supply or to any other output stage. This eliminates any concern of undesired currents flowing between any of the output stages.

The processor 46 included in the ICS 12 includes means (88 and 90) for selectively controlling the pulse width of the stimulation signals applied to the electrode 48. Such means preferably comprises a timing circuit capable of turning the stimulus current of a particular channel on and off with a time resolution of approximately one microsecond. Such means is preferably controlled by a command signal separate from the signals which set the current to each stimulus channel; the command signal controls the duration of current stimulus while the previously described signals control the stimulus current in each channel.

Further, the processor 46 included in the ICS 12 includes means for selectively controlling the frequency at which stimulating signals are applied to select ones of the electrodes. This is preferably accomplished by providing a signal frame (or set of signals to the multiplicity of electrodes) of varying length. The use of short frames allows a subset of channels to be refreshed or updated more often than would be possible if all channels were always updated by a fixed, long frame. Such reduced frame length may be implemented either as a frame length encoded in the frame data or (in the preferred implementation) as a unique end of frame signal.

In the processor 46, the voltage downconverter 58 generates three voltages of different value for powering different components in the ICS 12. The voltage downconverter may comprise a set of capacitors and switches so arranged to connect the capacitors alternately in series across the high voltage from the regulator 44 input and then in parallel to provide a lower voltage supply (3.5 volts in the preferred implementation). The storage or supply capacitors 60 may be charged to various multiples of the 3.5 volt supply by connecting their associated transfer capacitors to the appropriate points in the downconverter when the downconverter capacitors are connected in series.

The ICS 12 includes means for selectively receiving and responding to analog and/or pulsatile input data from the WP 16. Preferably, this is accomplished by using the stimulus current control signals to provide continuous analog control of stimulus and using a separate command signal to selectively control the "on" or "off" status of a given channel. The stimulus parameters of each channel are controlled independently of all other channels by means of separate signals within the data frame and separate configuration commands for each channel encoded in the command signal.

Further, the ICS 12 is capable of selectively stimulating the electrodes in a unipolar and/or bipolar configuration. This is accomplished by providing a set of command signals which affect separate bits for each channel in the output mode register 86. Via the output control logic 88, these bits independently configure the switches for each channel in the electrode switching matrix 66. The switches allow the current source FET 62 and storage capacitors 60 to be connected to pairs of electrodes (bipolar mode) or, alternatively, to individual electrodes and the indifferent electrode 49 via the indifferent electrode switches 92.

Figure 3:
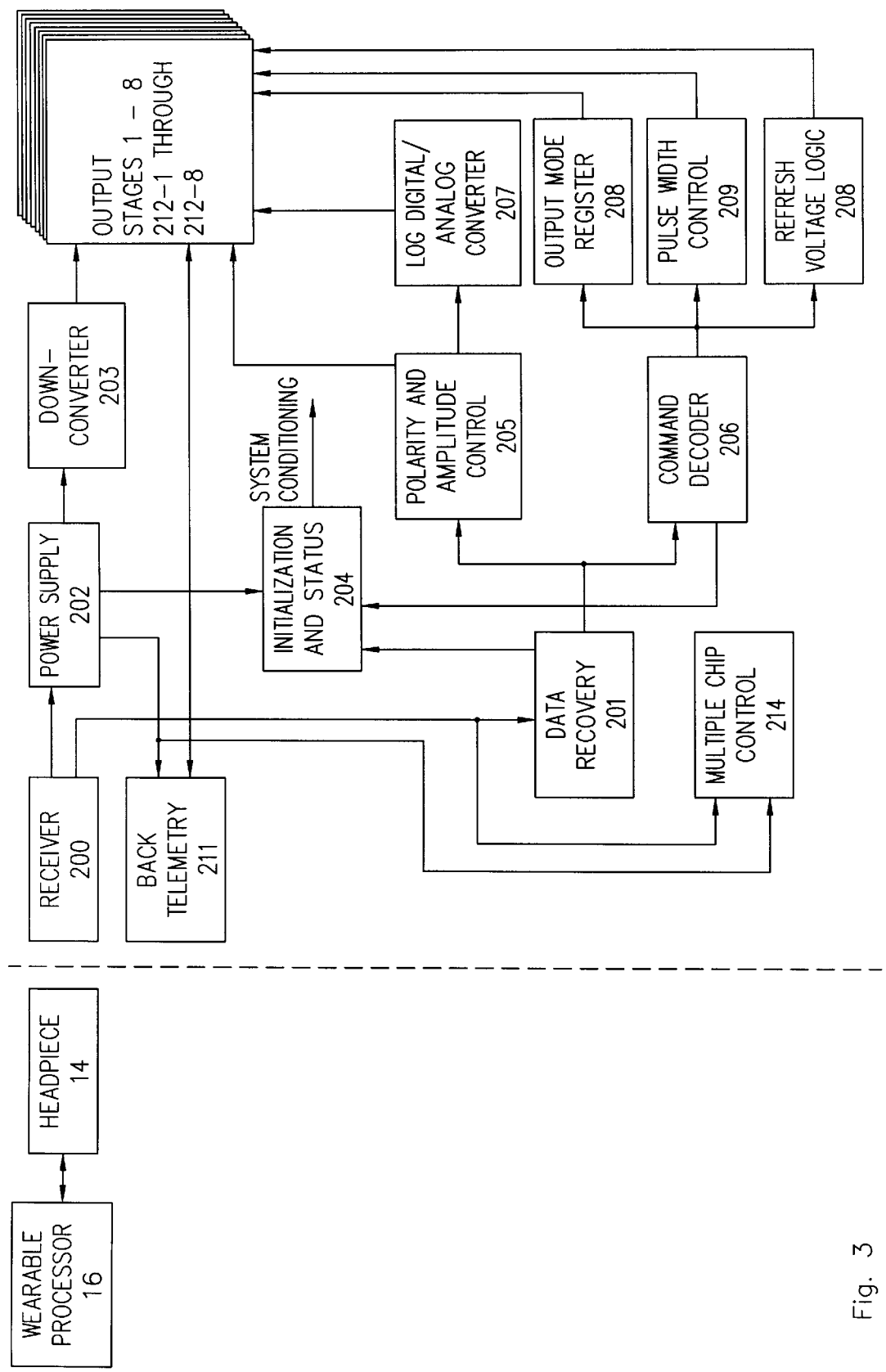
FIG. 3 is block diagram of second form of a cochlea stimulating system comprising a preferred embodiment of the present invention.

While FIG. 2 illustrates a basic ICS, FIGS. 3 and 4A–4H illustrate a preferred form of the ICS. FIG. 3 is a more general block diagram illustration of the system which is represented in greater detail in FIGS. 4A–4H. The majority of the active circuitry of the ICS may be imbedded in a custom chip which with other active and passive circuitry comprising the ICS may be supported on a substrate. The ICS illustrated in FIGS. 3 and 4A–4H comprises a receiver 200 for receiving an input signal generated in the WP 16 and transmitted by the headpiece 14. Preferably, such input is a Manchester-encoded data stream comprising an amplitude-modulated RF signal consisting of a serial sequence of 83 bits representing 9 words of 9 bits each plus a parity bit and an end-of-frame marker. A frame is defined as one such bit sequence and such frames are sent sequentially from the WP to the ICS. The first 8 words of each frame contain the digital amplitude and polarity information for output channels 1 through 8 in that order. The 9th word contains command information for the control of ICS configuration and functionality. The receiver 200 separates the incoming RF signal into a power signal transmitted to a power supply section 202 and data which is transmitted into a data recovery section 201. In the power supply section, power signals are generated for the ICS and, via a downconverter 203, are transformed into the voltage levels which provide power for the eight output stages indicated by numbers 212-1 through 212-8, one of which will be described in greater detail hereinafter.

The data signal extracted by the receiver 200 and transmitted to the data recovery section 201 is further processed within the data recovery section to provide input signals to an initialization and status control section 204, a polarity and amplitude control section 205, a command decoder section 206, and to a multiple chip control 214. The initialization and status control section 204 receives power from the power supply section 202 and establishes the control conditions of the other sections of the ICS upon system startup and upon detection of a system operating error by the status control section. The polarity and amplitude control section 205 determines the polarity of the output currents generated in the various output stages 212-1 through 212-8 and generates signals which are further processed in a log D-A converter section 207 to control the magnitude of current signals supplied by the outputs of the various output stages. In the command decoder section 206, the data signals are processed and decoded to form signals which (1) via an output mode register 208 control the status of the output stages as either unipolar or bipolar, (2) via a pulse width control 209 control the width of the output pulses supplied by the output stages when such stages are in a pulsatile mode and (3) via a refresh voltage logic 210 control the power applied to the output stages. In addition, the ICS includes a back telemetry section 211 which in response to signals from the command decoder 206 generates and transmits back to the WP status indicating and power control signals. The status signals indicate the status of the various elements within the ICS and voltages generated therein. The power control signals control the power of the transmitted signals and effect a power conservation by control of the level of the signals from the WP and by control of the refresh voltages from the downconverter 203 to the various output channels.

Still further, the illustrated ICS includes a multiple chip control section 214. Section 214 enables the chip included in the ICS to act as a "master" having the capacity to drive a plurality of identical "slave" chips mounted on the substrate thereby effecting a multiplication of the number of output stages.

Figure 4:
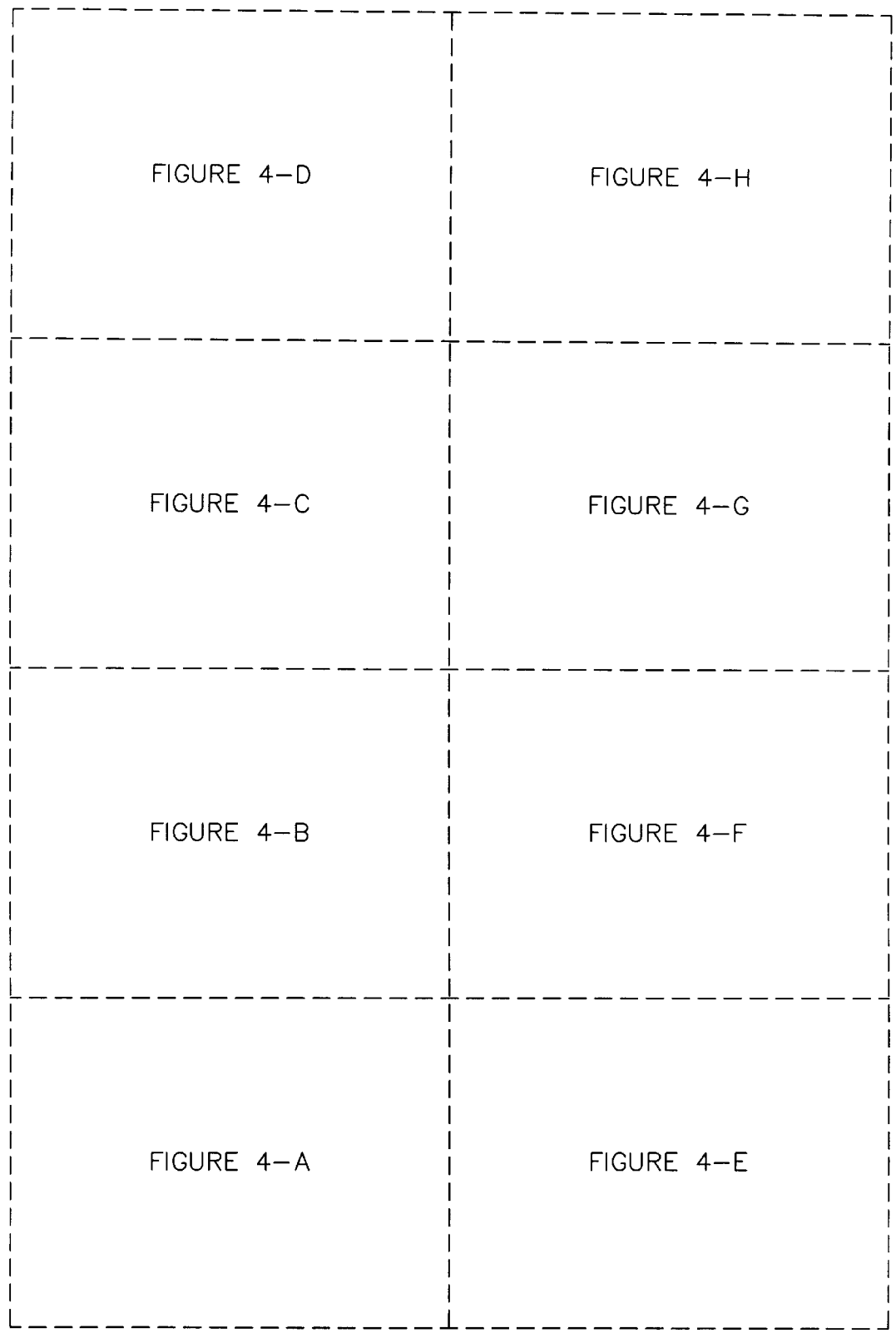
FIG. 4 is a block diagram of the layout of the system components and circuitry comprising the detailed showing of the ICS in FIGS. 4A–4H.

FIGS. 4A–4H, organized as set forth in FIG. 4, show details of the various system sections illustrated in FIG. 3, with subsections of the sections bearing the same numbers as set forth in FIG. 3 and with letters to denote the specific subsections, e.g., 201A, 201B, 201C and 201D are subsections of the data recovery section 201. The following detailed description of the sections and subsections comprising the system will begin with the receiver 200 and will continue through a description of the output stages 212-1 through 212-8 and multiple chip control 214 and will be followed by a description of the operation of the system comprising the described sections. Details of the frame structure, data word structure, and/or the transmission rate for the input signal from the WP and data signal extracted therefrom will be included in the description of the operation of the system.

Structure

Receiver 200

The receiver 200 illustrated in FIG. 4A is a conventional AM detector containing capacitors which implement a parallel resonant tuned circuit in conjunction with a main coil 50 followed by series connected power rectification and data detection diodes and energy storage capacitors to generate signals PDATA, NDATA, RAWDC, ZEROV and TANKV. PDATA and NDATA are differential signals generated across the data detection diodes and convey demodulated data to the data recovery section 201. RAWDC is DC voltage generated across the energy storage capacitors and is delivered to the input of a series regulator 202A in the power supply section 202. ZEROV is the reference voltage against which all other voltages are measured in the ICS. TANKV is derived from RAWDC via a resistive divider network in the receiver 200 and, as will be described in greater detail hereinafter, via a telemetry multiplexor 211B in back telemetry section 211 provides one of the power control signals which is an input to the back telemetry section.

Data Recovery 201

The data recovery section comprises four subsections: a data conditioner 201A, a clock decoder 201B, a serial to parallel converter 201C and a word strobe generator 201D. All analog and digital circuitry in the data recovery section 201 is of conventional design.

Within data conditioner 201A, the signals PDATA and NDATA from the receiver 200 provide the two inputs to an analog comparator. The output from the comparator is the signal MANDATA, which is the recovered version of the Manchester-encoded serial data stream transmitted by the WP. MANDATA is distributed to clock decoder 201B, serial to parallel converter 201C, as well as downconverter clock 203A to be discussed hereinafter.

In addition, within data conditioner 201A, the signal MANDATA is applied to the gate of a MOSFET switch which allows an on-chip capacitor to be charged in a pulsatile manner. A constant-current discharge path in parallel with the on-chip capacitor reduces the voltage to zero in the absence of the signal MANDATA. The voltage across the on-chip capacitor is buffered by three inverters to become the carrier detect signal, CARDET. CARDET is distributed to clock decoder 201B and to an initialization subsection 204B of the initialization and status control section 204.

In the clock decoder subsection 201B, the signal MANDATA is applied to an edge-detector circuit comprised of an XOR gate with an RC delay circuit preceding one of the inputs. Output pulses from the edge detector are the primary input to a phase-lock loop (PLL) circuit of conventional design which, by locking to the MANDATA pulse edges, generates the data clock signals CLKPH1 and CLKPH2. The clock signals comprise a two-phase non-overlapping clock system at a frequency of 1.1 MHz with a CLKPH1 pulse asserted during the first half of each bit time and a CLKPH2 pulse during the second half. Signals CLKPH1 and CLKPH2 are sent to the serial to parallel converter 201C, word strobe generator 201D, pulse width control 209 and an A/D converter 211C in back telemetry section 211.

Further, within clock decoder 201B, the timing of pulse edges in the signal MANDATA is compared to those of the local clock VCO in the PLL. In particular, a unique pulse with non-standard edge timing sent by the WP to mark an end-of-frame is sensed by a circuit of conventional design comprised of a D-type flip-flop and an XOR gate. This unique pulse results in the generation of the frame clock signal, PFRMCLK which is sent to serial to parallel converter 201C.

Additional circuitry of conventional design in the clock decoder 201B, comprising logic gates and binary counters, is used to generate a signal PLLLOCK. PLLLOCK is asserted so long as the PLL is locked to the signal MANDATA, CARDET is asserted, and, as will be described relative to a powerbad detector 204A in initialization and status control section 204, POWERBAD is negated. The signal PLLLOCK is sent to serial to parallel converter 201C and to parity error detector and initialization subsections 204C and 204B of section 204.

Serial to parallel converter 201C comprises logic gates, latches, D type flip-flops, counters and a shift register all of conventional design. Under control of the signal CLKPH1 and a signal DCENABLE from multiple chip control section 214, the serial data bits represented in the signal MANDATA are shifted into a 9-bit serial-in, parallel-out shift register. The first stage output of the shift register generates a serial bit stream signal SERDATA. The 9 outputs of the register are the source of the signal bus DATA (1–9) which is sent solely to a polarity and amplitude data latch 205A in section 205 and to a command latch 206A in command decoder 206.

In addition, within serial to parallel converter 201C, the signal PFRMCLK is gated with the clock signal CLKPH2 to generate a signal FRMCLK sent to pulse width control section 209 and a refresh voltage logic section 210.

Further, within serial to parallel converter 201C, the signal CLKPH1 is connected to the clock input of a 4-bit binary up-counter which is reset by FRMCLK. The counter and succeeding decoders and latches provide the signals XFERB and XFERC solely to an analog multiplexer 207C included in the log D-A converter section 207. Also, the bit 4 output of the counter is gated with CLKPH1 and CLKPH2 to produce the signal WORDTRCLK (word transfer clock) which provides a reset pulse to the counter as well as being sent to word strobe generator 201D, down converter clock 203A and a polarity and amplitude data latch 205A. The counter is also decoded to generate the signal AMPSYNC which is sent solely to pulse width control 209.

Word strobe generator 201D comprises logic gates, D type flip-flops and a 9-stage Johnson counter of conventional design. The signal WORDTRCLK provides the clock input to the Johnson counter. Signals CLKPH1, CLKPH2, FRMCLK and the output from stage 9 of the Johnson counter are combined to provide the reset signal for the counter. Outputs from the first 8 stages of the counter provide the 8-bit signal bus WSTRB. (1–8) with each line asserted during the appropriate word time during the data frame. WSTRB (1–8) is sent to analog multiplexer 207C, pulse width control 209 and back telemetry section 211. In addition, the output from stage 9 of the Johnson counter provides the signal WORD9CLK which is sent to command latch 206A and command decoder 206B.

Power Supply 202

As depicted in FIG. 4A, the power supply section 202 includes the series regulator 202A which includes a series regulating element such as a depletion-mode FET. In conjunction with a conventional voltage reference 202C and a conventional voltage regulator error amplifier 202B, the series regulator produces a precise negative 14 volts (NEG14) with respect to ZEROV for powering the balance of the ICS. The gate of the series regulating element in the regulator 202A is controlled by a signal REGCONT output from an operational amplifier located in a regulator error amplifier 202B, having as its inputs the output VREF of the voltage reference 202C and an attenuated version of NEG14, i.e., TAP14. The voltage reference 202C includes an off chip zener diode which is powered by the NEG14 line. The precision reference voltage VREF is generated across this zener diode.

Downconverter Section 203

As represented in FIGS. 4A and 4B, the downconverter section 203 comprises a downconverter clock 203A and a voltage downconverter 203B.

The downconverter clock 203A has as its inputs NEG14 and ZEROV from regulator 202A, MANDATA from data conditioner 201A, POWERBAD from powerbad detector 204A and WORDTRCLK from serial to parallel converter 201C and comprises two toggle flip-flops and a two-pole FET selector switch of conventional design. The two toggle flip-flops receive and divide by a factor of four, the signal MANDATA. During startup, since MANDATA is pulsing at 550 KHz, the resulting signal from the toggle flip-flop is a 137.5 KHz signal which is applied to one input of the two-pole FET switch. The other input to the two-pole switch is WORDTRCLK and the state of the switch is controlled by POWERBAD. Since, as will be described, POWERBAD is asserted during ICS startup, the 137.5 KHz signal is delivered as DOWNCLOCK during startup to the voltage down converter 203B whereas a level-shifted version of WORDTRCLK is sent out as DOWNCLOCK during normal ICS operation.

The voltage downconverter 203B comprises conventional logic gates and off-chip capacitors. It receives DC power (NEG14 and ZEROV) from series regulator 202A and a squarewave output signal DOWNCLOCK from the downconverter clock 203A. The squarewave is converted into a two-phase non-overlapping pair of clock signals in a conventional cross-connected logic gate and inverter circuit in the downconverter 203B. The two-phase clock signals drive a set of FET switches which establish the pattern of connections between and among a group of four off-chip capacitors 203-1 through -4.

During phase 1 of the clock signals, the four capacitors are connected in series across the −14 volt supply and each charges to a final value of −3.5 volts. At that time, output voltages of −3.5, −7.0, −10.5 and −14 volts are made available on outputs from the voltage downconverter 203B to each of the eight output stages 212-1 through 212-8 in the ICS, and, in particular, to each of the refresh voltage control subsections 212A included in such output stages.

During phase 2 of the clock signals, the four capacitors are connected in parallel and deliver charge to an off-chip storage capacitor 203-5 which is the source of the −3.5 volt logic supply. Also during phase 2, as a natural result of the parallel connection, the voltages on the four capacitors are equalized in preparation for the return to the series arrangement of the next phase 1.

Initialization and Status Control Section 204

The initialization and status control section 204 consists of digital circuitry and an analog comparator of conventional design to detect errors and to set the internal conditions of system circuitry on system startup and upon error detection by this section. Section 204 is made up of three subsections: a powerbad detector 204A, an initialization subsection 204B, and a parity error detector 204C.

The powerbad detector 204A comprises an analog comparator having the −3.5 volt output from the voltage downconverter 203B presented to one of its inputs. The other input to the comparator is the reference voltage, VREF, coming from power supply section 202. The comparator operates on the −3.5 volts and VREF to generate an output POWERBAD which is asserted when the −3.5 volt supply is below normal operating potential, such as during startup. Thus, during the initial phase of startup, the POWERBAD signal is asserted. The signal POWERBAD is used to force a known logic condition on circuitry within initialization subsection 204B and is also sent to the downconverter clock 203A and to the data recovery section 201 for the same purpose. For example, while POWERBAD is asserted, the output stages 212-1 through 212-8 are disabled. This is accomplished by POWERBAD resetting a flip-flop within 204B to negate a signal OUTENABLE, the assertion of which is required to enable any of the output stages. Then, upon negation of POWERBAD, assertion of CARDET from data conditioner 201A, PLLLOCK from clock decoder 201B and CONNECT from command decoder 206B, the flip-flop is set and OUTENABLE is asserted to enable the output stages 212.

Similarly, and as will be described again hereinafter, the assertion of a signal PALARM from parity error detector 204C will result in a disabling of the output stages 212 via a negation of Outenable. In this regard, parity error check is made at the end of each frame to assure that the total number of "ones" in the data stream to the ICS is even. The parity error detector 204C comprises a combination of logic gates and flip-flops of conventional design and is based on a D type flip-flop which is clocked by the serial bit data stream SERDATA from signal to parallel converter 201C. The state of the flip-flop at the end of the frame indicates whether the received number of one bits was odd or even. The resulting state of the D type flip-flop is then transferred to a holding flip-flop whose output generates the parity error signal PALARM which is connected to the initialization subsection 204B.

Initialization subsection 204B comprises a combination of logic gates of conventional design and receives input signals CARDET from clock decoder 201B; PALARM from parity error detector 204C; DISCON, CONNECT, and ALLZERO from command decoder 206B, PLLLOCK from clock decoder 201B and POWERBAD from POWERBAD detector 204A. CARDET, PALARM, PLLLOCK and POWERBAD have been described. The manner in which such input signals DISCON, CONNECT and ALLZERO are generated will be described hereinafter relative to section 206. Output signals generated by the initialization subsection 204B are CARON, OUTENABLE, RESETERR, and SYSRESET. In subsection 204B, the signal CONNECT sets a latch flip-flop to assert the output signal OUTENABLE at pulse width control 209. Input signals DISCON and ALLZERO are combined in logic gates within subsection 204B to generate the output RESETERR which goes from 204B to parity error detector 204C to reset the parity error detector flip-flop. Signals PALARM, DISCON, ALLZERO, PLLLOCK and POWERBAD are combined in logic gates within 204B such that when any of these signals indicate a problem, a disconnect command output signal SYSRESET is generated and functions as a general reset signal for all the circuitry in the ICS. In this regard, SYSRESET, when asserted will reset the ICS circuitry to its initial state ready for restart in response to system startup data from the WP. Signals CARDET and PLLLOCK asserted and signals POWERBAD and PALARM not asserted combine in gates in 204B to generate the output signal CARON. CARON goes off-chip to turn on the back telemetry carrier signal, at a telemetry transmitter 211E of the back telemetry section 211. As will be described hereinafter, the absence of the back telemetry carrier signal is detected in the WP as an indication of a system defect in the ICS. The WP will initiate a restart of the ICS and will continue in that mode until the back telemetry carrier signal is again detected.

Polarity and Amplitude Data Latch Section 205

The polarity and amplitude data latch section 205 comprises amplitude data latch 205A and a zero current control 205B. The latch 205A consists of a conventional 9-bit latch which receives data bit inputs from a 9-bit bus DATA (1–9) from the serial to parallel converter 201C in addition to WORDTRCLK also generated in 201C. WORDTRCLK causes the input data bits DATA (1–9) to be latched and then held until replaced by a new set of incoming data. Output from the 9-bit latch consists of an 8-bit wide data bus signal AMPDATA (1–8) and a 9th bit defining a single line POLARITY which goes directly to output stages 212-1 through 212-8. AMPDATA (1–8) goes from latch 205A to the zero current control 205B and to the logarithmic D-A converter in section 207, and as described more specifically hereinafter, to the internal subsection 207B.

The zero current control 205B comprises logic gates of conventional design. The signal bus AMPDATA (1–8) from amplitude data latch 205A is decoded in an 8 input gate such that the output of the gate is asserted only when all 8 bits are at logic 0. This corresponds to a requested output current amplitude of zero. The signal POLARITY from the latch 205A is combined with AMPDATA (1–8) to generate two (2) complimentary output signals ZERO and SHORT. SHORT is asserted when AMPDATA (1–8) is all zeroes and POLARITY is 1 and, conversely, ZERO is asserted when AMPDATA (1–8) is all zeroes and POLARITY is 0 (zero).

Command Decoder 206

The command decoder section 206 comprises digital logic circuitry of conventional design and consists of two subsections: command latch 206A and command decoder 206B. The command latch 206A is similar to latch 205A discussed above in that it is a 9-bit latch with input data coming from the 9-bit bus DATA (1–9) from serial to parallel converter 201C. In command latch 206A, DATA (1–9) is caused to be latched by signal WRD9CLK from the word strobe generator 201D to develop a 9-bit bus WORD9 (1–9) output which is maintained until replaced by a new ninth word command. WORD9 (1–9) connects directly to the command decoder 206B which consists of logic gates to decode the various functions from the 9-bit combinations on the output bus. The following table depicts the content of WORD9 and the outputs generated by the various function codes contained in bits 6–8 of WORD9.

TABLE 1

| 8 | 7 | 6 | 5 | 4 | 3 | 2 | 1 | 0 |
|---|---|---|---|---|---|---|---|---|
| Function code | | | Value C B A | | | Channel Number | | |

| Func. Code | Outputs | Description |
|---|---|---|
| 000 | ALLZERO, DISCON, CONNECT | global control |
| 001 | FUNC2 | output control |
| 011 | FUNC4 | normal back telemetry read |
| 100 | FUNC5 | inverted back telemetry read |

TABLE 1-continued

| 8 | 7 | 6 | 5 | 4 | 3 | 2 | 1 | 0 |
|---|---|---|---|---|---|---|---|---|
| Function code | | | Value C B A | | | Channel Number | | |

| Func. Code | Outputs | Description |
|---|---|---|
| 110 | FUNC7 | refresh voltage control |
| 111 | FUNC8 | output pulse width control |

In addition, command decoder 206B receives input signals RFMAIN from refresh voltage logic 210, PFMAIN from pulse width control 209 and WORD9CLK and WSTRB1 from the word strobe generator 201D. Output signals from 206B which exit the command decoder 206 consist of logic gate output signals CONNECT, DISCON, ALLZERO, FUNC2, FUNC4, FUNC5, FUNC7 and FUNC8.

As previously described, the signals CONNECT, DISCON and ALLZERO exiting the command decoder 206 provide inputs into the initialization section 204. FUNC2 through FUNC8 are function decodes which provide inputs to the various sections which they control on a command basis. The signal FUNC2 is the primary enabling signal going from the command decoder to the output mode register 208. Signals FUNC4 and FUNC5 are connected directly to the back telemetry section 211 (telemetry function decoder 211A and A/D converter 211C) to control its function. FUNC7 is directly and solely connected to the refresh voltage logic 210 to provide enabling for the refresh voltage control portion. FUNC8 is connected directly and solely to pulse width control 209 to enable that function to take place.

Logarithmic D/A Converter 207

The logarithmic D/A converter section 207 consists of conventional analog and digital circuitry, with the exception of a logarithmic D/A converter subsection 207B which is the subject of U.S. Pat. No. 4,931,795 issued Jun. 5, 1990 and assigned to the same assignee as this invention. The logarithmic D/A converter 207 consists of three subsections: a current reference generator 207A, the logarithmic D/A converter subsection 207B, and an analog multiplexer 207C. The current reference generator 207A receives a voltage input VREF from the voltage reference 202C and utilizes that reference voltage to generate reference output current signals ADIREF and IREF. ADIREF is a fixed current supply to A/D converter 211C while IREF provides the input current to the logarithmic D/A converter 207B which includes multiplicative stages of current mirrors controlled by the 8-bit data bus AMPDATA (1–8) from the data latch 205A. Output signals from the logarithmic D/A converter subsection 207B are control voltages IPOSCON and INEGCON connected to the analog multiplexer subsection 207C. The multiplexer is controlled by signals XFERB and XFERC from the serial to parallel converter 201C and an 8-bit bus signal WSTRB (1–8) from the word strobe generator 201D. Outputs from the analog multiplexer are distributed to, and control, each of the current sources 212B in the eight output circuits 212-1 through 212-8 as signals IPOS (1–8) and INEG (1–8). Thus, the output current from each of the eight output stages 212-1 through 212-8 are controlled individually, separately and sequentially.

Output Mode Register 208

The output mode register 208 contains 24 transparent latches of conventional design arranged in 3 banks of 8 latches each. The 8 latches in the first bank give rise to an 8-bit bus AMONO (1–8) and likewise the remaining 2 banks generate bus signals BMONO (1–8) and DRC (1–8). AMONO(1), BMONO(1) and DRC(1) connect to output stage 212-1 and the rest of the bus signals are distributed to the other 7 output stages in a like manner.

Only upon assertion of function code signal FUNC2 from the command decoder 206B can the bit pattern in the latches of the register 208 be modified. More particularly, under control of pulse signal WSTRB1 from word strobe generator 201D, the low-order 3 bits of the 9-bit bus signal WORD9 (1–9) from the command latch 206A are decoded in a conventional 3-to-8 decoder. The decoder has each of its 8 output lines connected to and selectively enabling one latch in the same position in each of the three banks comprising the register 208 to effect a selective modification of the bit pattern in the register according to the pattern of the low order 3 bits. The middle 3 bits of WORD9 (1–9) are each connected to a single one of the 3 banks and enable the data inputs to all 8 latches in each of the three banks comprising 208. The high-order 3 bits in WORD9 (1–9) are not used in section 208.

Pulse Width Control Section 209

The pulse width control section 209 comprises logic gates, latches, D type flip-flops, counters and decoders of conventional design. The signals FUNC8 from command decoder 206B in conjunction with FRMCLK, CLKPH1 and CLKPH2 enables the operation of this section and causes the contents of two sequential 9th words to be latched from the bus signal WORD9 (1–9) into one of two buffers under control of a bit 5 in the first WORD9. The contents of the two WORD9 commands are diagrammed below:

TABLE 2

| WORD9 | | | | |
|---|---|---|---|---|
| First WORD9 | 876 | 5 | 43 | 210 |
| | 111 | E | FF | CCC |
| Second WORD9 | 8 | 7 | 6543210 | |
| | X | D | NNNNNNN | |

E—EDGE CONTROL BUFFER NUMBER [0,1]
FF—EDGE EXECUTION FRAME NUMBER [00,01,10,11]
CCC—CHANNEL NUMBER [000–111 = CH1–CH8]
X—DON'T CARE
D—DIRECTION OF EDGE [0 = ON TO OFF, 1 = OFF TO ON]
NNNNNNN—COUNT TO OCCURRENCE OF EDGE [0–84]

As depicted in Table 2, requested stimulus output pulse edges will occur at the bit time specified in second WORD9 bits 0–6 above, during the frame time according to the command specified in the first WORD9 bits 3 and 4. This is accomplished by using such data bits to preset two down-counters which are decremented by the signal CLKPH1 from the clock decoder 201B and FRMCLK from the serial to parallel converter 201C respectively. Channel select bits 0–2 in the first WORD9 are latched and decoded to allow the passing of edge information only to the requested output channel as represented in the 8-bit signal bus PWC (1–8). The signal OUTENABLE from initialization 204B is gated with all bits of PWC (1–8) and must be asserted to enable any PWC (1–8) line to be asserted. Assertion of at least one PWC line is required for any stimulation signal to occur (see Table 6 herein).

Refresh Voltage Logic Section 210

Refresh voltage logic 210 comprises logic gates and latches of conventional design. The signal bus WORD9 (1–9) is gated into 8 pairs of such latches. The outputs from each one of each pair of latches is represented as one line in each of the two output bus signals RVO (1–8) and RV1 (1–8) which are sent to a refresh voltage control 212A included in each of the output stages in section 212.

Since at least 16 bits are required to establish 4 possible refresh voltage levels across 8 channels, the refresh system is controlled by 2 consecutive 9th word commands of 9 bits each. The format of these 2 command words is shown below:

TABLE 3

| | Word9 | | | | |
|---|---|---|---|---|---|
| First WORD9 | 876 | 5 | 43 | 21 | 0 |
| | 110 | stage 1/2 select | stage 1/2 RV | stage 3 RV | stage 4 RV |
| Second WORD9 | 8 | 76 | 54 | 32 | 10 |
| | stage 4 RV | stage 5 RV | stage 6 RV | stage 7 RV | stage 8 RV |

As depicted in Table 3 above, the first WORD9 consists of the function code for refresh voltage control (110 in bits 8–6), a stage 1 or 2 select code (bit 5: 1=stage 1, 0=stage 2) which determines whether stage 1 or stage 2 will be updated at this time, the stage 1 or 2 refresh voltage level code RV (bits 3 and 4), the stage 3 refresh level code (bits 1 and 2) and the high-order bit of the refresh level code for stage 4. The second WORD9 also consists of 9 bits with bit 8 representing the low-order bit of the refresh level code for stage 4 and the remaining 8 bits representing the 2-bit refresh level codes for stages 5 through 8. Note that stages 3 through 8 are always updated but only stage 1 or stage 2 may be manipulated by a given command. Updating both stages 1 and 2 requires two separate double WORD9 refresh voltage commands. The 2-bit RV codes and the refresh voltage levels associated with them are shown below:

| Code | | |
|---|---|---|
| RV1 | RV0 | refresh voltage |
| 0 | 0 | −14 volts |
| 0 | 1 | −7.0 volts |
| 1 | 0 | −3.5 volts |
| 1 | 1 | −10.5 volts |

Backtelemetry Section 211

The backtelemetry section 211 comprises telemetry function decoder 211A, a telemetry multiplexer 211B, an A/D converter 211C, a telemetry modulator 211D and a telemetry transmitter 211E.

Decoder 211A comprises logic gates, latches and decoders of conventional design receiving as inputs WSTRB (1–8), WORD9 (1–9), FUNC4 and FUNC5. Within decoder 211A signals WSTRB8 and WSTRB1 are combined to create signal WSTRB9 which is asserted from the end of WSTRB8 until the beginning of WSTRB1 and sent to the A/D converter 211C and telemetry modulator 211D. Signals FUNC4 and FUNC5 are the primary activation signals for decoder 211A and cause the 6 low-order bits in the input bus signal WORD9 (1–9) to be latched, decoded and gated to control output signals applied to: indifferent electrode switch 212D (IECLOSE); bus MUXCTRL (1-23); and lines identified as VRTPWR, RLOCTRL and RHICTRL (to telemetry multiplexer 211B), ADPWR, and SH2X1, SH2X3, SH2X10 and SH1X10 (to A/D converter 211C) to control functions in subsections 211B and 211C as shown in the tables below:

TABLE 4A

Six low order bits

| WORD9 543 210 | Output Signal from 211A | Description of Function Activated in MUX 211B |
|---|---|---|
| 001 000 | MUXCTRL1 | VOUTA1 vs VOUTB1 |
| 001 001 | MUXCTRL2 | VOUTA2 vs VOUTB2 |
| 001 010 | MUXCTRL3 | VOUTA3 vs VOUTB3 |
| 001 011 | MUXCTRL4 | VOUTA4 vs VOUTB4 |
| 001 100 | MUXCTRL5 | VOUTA5 vs VOUTB5 |
| 001 101 | MUXCTRL6 | VOUTA6 vs VOUTB6 |
| 001 110 | MUXCTRL7 | VOUTA7 vs VOUTB7 |
| 001 111 | MUXCTRL8 | VOUTA8 vs VOUTB8 |
| 010 000 | MUXCTRL9 | ICP1 vs NRV_1 |
| 010 001 | MUXCTRL10 | ICP2 vs NRV2 |
| 010 010 | MUXCTRL11 | ICP3 vs NRV3 |
| 010 011 | MUXCTRL12 | ICP4 vs NRV4 |
| 010 100 | MUXCTRL13 | ICP5 vs NRV5 |
| 010 101 | MUXCTRL14 | ICP6 vs NRV6 |
| 010 110 | MUXCTRL15 | ICP7 vs NRV7 |
| 010 111 | MUXCTRL16 | ICP8 vs NRV8 |
| 011 XXX | RLOCTRL | Output current monitor, high range |
| 100 XXX | RHICTRL | Output current monitor, low range |
| 101 000 | MUXCTRL17 | ZEROV vs ZEROV |
| 101 001 | MUXCTRL18 | ZEROV vs 3.5 |
| 101 010 | MUXCTRL19 | ZEROV vs VREF |
| 101 111 | MUXCTRL20 | EXTP vs EXTN |
| 101 100 | MUXCTRL21 | ZEROV vs TAP14 |
| 101 101 | MUXCTRL22 | NEG14 vs TANKV |
| 101 110 | MUXCTRL23 | ZEROV vs VRTV (int. voltage) |
| 101 111 | | no operation |

TABLE 4B

Six low order bits

| WORD9 543 210 | Output Signal from 211A | Description of Function Activated in A/D Converter 211C |
|---|---|---|
| 111 000 | SH2 × 1 | set gain to × 1 (default) |
| 111 001 | SH2 × 1,3 | set gain to × 3 |
| 111 010 | SH2 × 1,10 | set gain to × 10 |
| 111 011 | | no operation |
| 111 100 | SH1 × 10,SH2 × 1 | set gain to × 10 (redundant) |
| 111 101 | SH1 × 10,SH2 × 3 | set gain to × 30 |
| 111 110 | SH1 × 10,SH2 × 10 | set gain to × 100 |
| 111 111 | | no operation |

TABLE 4C

| Six Low Order Bits | Description of Function Activated in 211B,C,D | | |
|---|---|---|---|
| 543 210 | IECLOSE | VRTPWR | ADPWR |
| 110 000 | open | off | off |
| 110 001 | open | off | on |
| 110 010 invalid state | | | |
| 110 011 | open | on | on |
| 110 100 | closed | off | off |
| 110 101 | closed | off | on |
| 110 110 invalid state | | | |
| 110 111 | closed | on | on |

The telemetry multiplexer subsection (telemetry MUX 211B) comprises 25 level shifters connected to 25 pairs of transmission-gates of conventional design which allow one and only one pair of MUX input signals to be connected to the pair of output lines, MUXOUT+ and MUXOUT−. This pair of output lines convey the differential signal to be measured and are connected to the A/D converter 211C.

A/D converter 211C comprises logic gates, level shifters, transmission-gates, switched capacitor amplifiers and comparators of conventional design arranged in 2 stages. The first stage has a default gain of 1 and can be changed to a gain of 10 by signal SH1X10. The second stage has selectable gains of 1, 3 or 10 as set by signals SH2X1, SH2X3 and SH2X10, respectively. Signal ADPWR from decoder 211A is used to turn on operating power to the amplifiers and the comparator in subsection 211C only when back telemetry has been requested by the WP WORD9 commands. This manner of operation is power-conservative.

In addition, in the converter 211C signals FUNC4 and FUNC5 are connected to the set and reset inputs of a flip-flop which has as its Q output a signal NORMPOL. Assertion of FUNC4 results in NORMPOL true and assertion of FUNC5 causes negation of NORMPOL. Within the converter 211C, NORMPOL is used to direct the converter to take a normal or inverted sample of the signal presented to it via the telemetry MUX 211B. In addition, NORMPOL is sent to the telemetry modulator 211D.

Further, in converter 211C, the signals WSTRB (1–8) from the word strobe generator 201D and WSTRB9 from telemetry function decoder 211A are combined in logic gates and level shifters to generate a multiphase clock for controlling switch timing in a switched capacitor amplifier circuit which samples, holds and conditions the voltage to be measured. A reference level for the samples is established by signal VREF.

More particularly, the voltage sample is delivered to a single-slope A/D converter of conventional design which comprises a comparator along with a ramp generator. The ramp generator uses the fixed current ADIREF to charge an on-chip capacitor. The comparator senses equality of the ramp voltage and the sample voltage, terminating the conversion cycle and causing the contents of a 6-bit counter driven by the signal CLKPH1 to be latched. The 6-bit latch output is the bus signal ADCOUNT (1–6) which is sent to telemetry modulator 211D.

Subsection 211D comprises 7 tri-state buffers of conventional design. The 7 buffers are connected to the output line DATAOUT and represent the 6 bits resulting from the A/D conversion plus a 7th bit which indicates polarity. The 7 bits are placed on the common output line DATAOUT in a sequence controlled by WSTRB (2–8) following a logic 1 sent during the WSTRB1 on-time and preceding a logic 0 sent during the WSTRB9 on-time. Thus, 9 bits are conveyed to a conventional off-chip telemetry transmitter 211E and thence to the WP in synchrony with one full data frame sent to the ICS by the WP. As previously described, the transmitter 211E is enabled for such transmission by the signal CARON from initialization 204B.

Output Stages 212—1 through 8

Output stages 1–8, section 212 (1–8), comprise 8 identical circuits. The table below summarizes the electrical connections to the output stages 1–8 comprising single lines connected to all 8 stages in parallel as well as 8-line buses with an individual line connected to each of output stages 1–8.

TABLE 5

SUMMARY OF CONNECTIONS TO OUTPUT STAGES 1 THROUGH 8

| Single lines connected to all eight stages in parallel: | 8 line buses with 1 line connected to each output stage 1 through 8: |
| --- | --- |
| Zero V | RV0 (1–8) |
| −14 V | RV1 (1–8) |
| −10.5 V | IPos (1–8) |
| −7 V | INEG (1–8) |
| DCLKPH1 | PWC (1–8) |
| DCLKPH2 | AMONO (1–8) |
| ZERO | BMONO (1–8) |
| SHORT | DRC (1–8) |
| POLARITY | OUTA (1–8) |
| INDCOM | OUTB (1–8) |
|  | VOUTA (1–8) |
|  | VOUTB (1–8) |
|  | ICP (1–8) |
|  | NRV (1–8) |

Output stage 1 will be discussed below as representative of all 8 stages. Output stage 1, section 212-1, comprises a refresh voltage control 212A, a current source 212B, an electrode switching matrix 212C and an indifferent electrode switch 212D. The refresh voltage control 212A comprises a conventional switching matrix, like the matrix 212C, in addition to level shifters connected to input circuitry to distribute two different logic levels defined by −3.5 and −14 volts within the refresh voltage control 212A and to the circuits that communicate with the refresh voltage control. As indicated, inputs to the refresh voltage control 212A include the 4 power supply voltage levels (−14V, −10.5V, −7.0V, −3.5V) along with signals DCLKPH1 and DCLKPH2 from the downconverter 203B. Signals RV1 and RV0 from the refresh control logic 210 provide a 2-bit code to logic gates connected to an intermediate charge storage device for the output stage 1, comprising "flying" capacitor CF1. Signals RV0 and RV1 operate on the logic gates to select one of the four power supply voltages to charge CF1 during assertion of signal DCLKPH1. During assertion of signal DCLKPH2, capacitor CF1 is disconnected from the selected power supply voltage and is connected in parallel with and transfers charge to a capacitor CRV1 via lines PRV1 and NRV1. Such switched capacitor circuitry impresses the voltage of CF1 on storage capacitor CRV1. CRV1 then functions as a floating power source for output stage 1. In this regard, it is the use of the intermediate charge storage device, CF1, alternately connected to the power supply voltages and to CRV1 of output stage 1, that provides electrical isolation for the output stage 1.

As previously described with respect to Refresh Voltage Logic Section 210, more than 9 bits are required to specify which one of the four refresh voltages is to be selected for each of the 8 isolated output stages. Therefore, two ninth-word commands are issued by the WP in two frames in sequence, processed in the ICS, and produce two WORD9 commands from command latch 206A. To control the refresh voltage for Stage 1, the first WORD9 command consists of the refresh voltage function control 110 in bits 8–6, a stage 1 select code 1 in bit 5, a stage 1 refresh voltage level code in bits 3 and 4, a stage 3 refresh level code in bits 1 and 2 and a high-order bit of the refresh level code for stage 4. The second WORD9 command includes the refresh level codes for stages 5 through 8. Note that stages 3 through 8 are always updated but only stage 1 or stage 2 may be manipulated by a given command. Updating both stages 1 and 2 requires two 2-word refresh voltage commands. The 2-bit refresh voltage level codes for stage 1 in bits 3 and 4 of the first WORD9 (RV1 and RVO) and the refresh levels associated therewith are shown below:

| Code | | |
| --- | --- | --- |
| RV1 | RV0 | refresh voltage |
| 0 | 0 | −14 volts |
| 0 | 1 | −7.0 volts |
| 1 | 0 | −3.5 volts |
| 1 | 1 | −10.5 volts |

The refresh voltage control 212A has a pair of input latches to hold the 2-bit level codes. The latches are always reset to the 00 (−14 volt) state at startup by the startup reset signal SYSRESET from the initialization section 204B and remain in that condition unless overwritten by a refresh voltage command. Thus, the highest available source voltage is automatically selected for all channels. However, the source voltage can be reduced on a channel-by-channel basis as indicated by back-telemetry data related to the power required for each channel. Such reduction of the source voltage will minimize power dissipation in the current source 212B in the affected output stage and thereby reduce power dissipation in the ICS 12.

Within current source 212B, power signal NRV1 from refresh voltage control 212A is connected to the source of a conventional MOSFET device comprising the current source. Connected to the drain of the MOSFET device is the output line −IN1 which connects to the electrode switching matrix 212C and is one line of the signal bus ICP (1–8) connected to the telemetry MUX 211B. Similarly, signal NRV1 is one line of the signal bus NRV (1–8) also connected to subsection 211B.

The gate-to-source voltage of the MOSFET device is controlled by signals IPOS1 and INEG1 respectively from analog multiplexer 207C, with such signals being applied to the device through transmission gates in the analog multiplexer controlled by signals XFERB and XFERC from converter 2D1C. The gate-to-source voltage so applied in a periodic manner is stored in a capacitor associated with the gate of the MOSFET device and remains operative between the refresh episodes. The refresh episodes are sequentially distributed across all 8 output stages in a non-overlapping manner so that only one current source 212B is connected via multiplexer 207C to the ICS circuitry at any time. The seven non-selected current sources are isolated from each other and the rest of the ICS circuitry by the off-resistance of the transmission gates in multiplexer 207C.

Electrode switching matrix 212C is the final subsection leading to the output coupling capacitors CA1 and CB1 which are connected to the stimulating electrodes. The circuitry in this subsection comprises logic gates, transmission gates, latches and level shifters of conventional design. Electrical isolation of the output stage is maintained in the switching matrix 212C since the various control signals for the matrix are applied only to the gates of MOSFET devices which comprise the transmission gates and which directly control the functions described hereinafter.

In particular, two transmission gates are connected between the signal lines +IN1 and −IN1 upon their entry into the matrix 212C. One of the transmission gates is of low on-resistance and is latched by the signal SHORT from the zero current control 205B. The other transmission gate is a high on-resistance device which is turned on by the signal DRC1 from the output mode register 208.

Signals +IN1 and −IN1 are connected to outputs OUTA1, OUTB1, VOUTA1, VOUTB1 and INDCOM via 10 transmission gates in the matrix 212C. The transmission gates are controlled by logic gates driven by input signals AMONO1 and BMONO1 from the output mode register 208, PWC1 from pulse width control 209 and POLARITY from amplitude data latch 205A. The connection patterns are shown in the table below.

where n is the number of slave chips and 1 represents the frame associated with the master chip. Note that each standard frame included in the long frame comprises an end of frame pulse (depicted in black) and that the long frame is terminated in a unique marker that signals the end of the long frame. Thus in multiple chip operation, the format of

TABLE 6

| INPUT SIGNALS | | | | CONNECTION | | | PATTERN | | DESCRIPTION |
|---|---|---|---|---|---|---|---|---|---|
| AMONO1 | BMONO1 | PWC1 | POLARITY | CONNECT TO OUTA1 | CONNECT TO OUTB1 | CONNECT TO INDCOM | CONNECT TO VOUTA1 | CONNECT TO VOUTB1 | OF CONNECTION PATTERN |
| 0 | 0 | 1 | 1 | +IN1 | −IN1 | NONE | OUTA1 | OUTB1 | BIPOLAR NORMAL |
| 0 | 0 | 1 | 0 | −IN1 | +IN1 | NONE | OUTA1 | OUTB1 | BIPOLAR INVERT |
| 1 | 0 | 1 | 1 | +IN | NONE | −IN | OUTA1 | INDCOM | MONOA NORMAL |
| 1 | 0 | 1 | 0 | −IN | NONE | +IN | OUTA1 | INDCOM | MONOA INVERT |
| 0 | 1 | 1 | 1 | NONE | +IN1 | −IN | OUTB1 | INDCOM | MONOB NORMAL |
| 0 | 1 | 1 | 0 | NONE | −IN1 | +IN | OUTB1 | INDCOM | MONOB INVERT |
| 1 | 1 | X | X | NONE | NONE | NONE | OUTA1 | OUTB1 | DISCONNECT |
| X | X | 0 | X | NONE | NONE | NONE | X | X | DISCONNECT |

Please note that selection of any monopolar mode will eliminate the electrical isolation of that particular output stage via the common connection to INDCOM.

Bus signals VOUTA (1–8) and VOUTB (1–8) from the matrix 212C, ICP (1–8) from current source 212B and NRV (1–8) from refresh voltage control 212A are all connected to the telemetry multiplexer 211B as previously described. Output line INDCOM from the matrix 212C is connected to the indifferent electrode switch 212D.

Within the switch 212D, the signals OUTENABLE from initialization 204B and IECLOSE, RLOCTRL and RHICTRL from telemetry function decoder 211A control the connection between INDCOM and the indifferent electrode via line INDELEC. Assertion of OUTENABLE and IECLOSE activates a transmission gate within the switch 212D which then connects INDCOM directly to INDELEC. Further, assertion of RLOCTRL or RHICTRL from telemetry function decoder 211A places off-chip resistor RLO or RHI, respectively, in a series connection between INDCOM and INDELEC. Stimulus current flowing through the selected resistor generates the voltage output signal ILO or IHI with respect to INDELEC. Such signal is proportional to stimulus current in the monopolar mode and is sent to telemetry MUX 211B.

Multiple Chip Control 214

In the preferred embodiments thus far described, the ICS comprises a single chip. However, multiple chips of the same or similar circuitry may be usefully employed in a human tissue stimulator. In such an embodiment, a circuit 214 at the input of each chip permits the interconnection of several chips into one functional unit by making one of the chips a master device which receives data and clock signals and then distributes such signals to all the slave chips. In this manner a large number of chips may be connected together forming a system with a large number of output channels, e.g., 16 monopolar channels times the number of chips. Such an embodiment, for example, with two chips, one master and one slave, provides twice the number of channels and requires twice the number of words per frame. In such an embodiment, a total of 18 words per frame instead of the basic 9 words per frame is required since the two chips are in series.

Figure 5A:
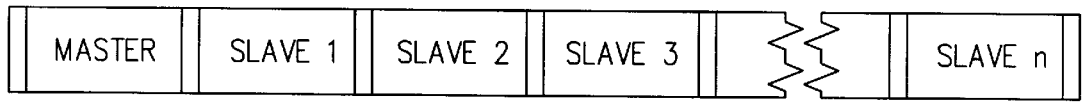
FIG. 5A depicts a long data frame useful in multiple chip configurations for the stimulating system, the long frame comprising a series of n+1 data frames, the first frame being designated as a master frame and the subsequent frames being designated as slave frames 1 through n. The number of data frames comprising the long data frame corresponds to the number of chips included in the system.

FIG. 5A depicts a long data frame for multiple chip operation including n+1 standard frames per long frame, the data transmission is extended by one level. A set of data consists of bits, words, and standard frames embedded in a long frame. As in the regular operation of an ICS previously described, one word consists of 9 bits and one frame consists of 9 words. However, one long frame consists of as many frames as there are chips participating in the multiple chip operation. The beginning (or end) of a long frame is defined by a long frame pulse that has a duration of two regular frame pulses.

Figure 5B:
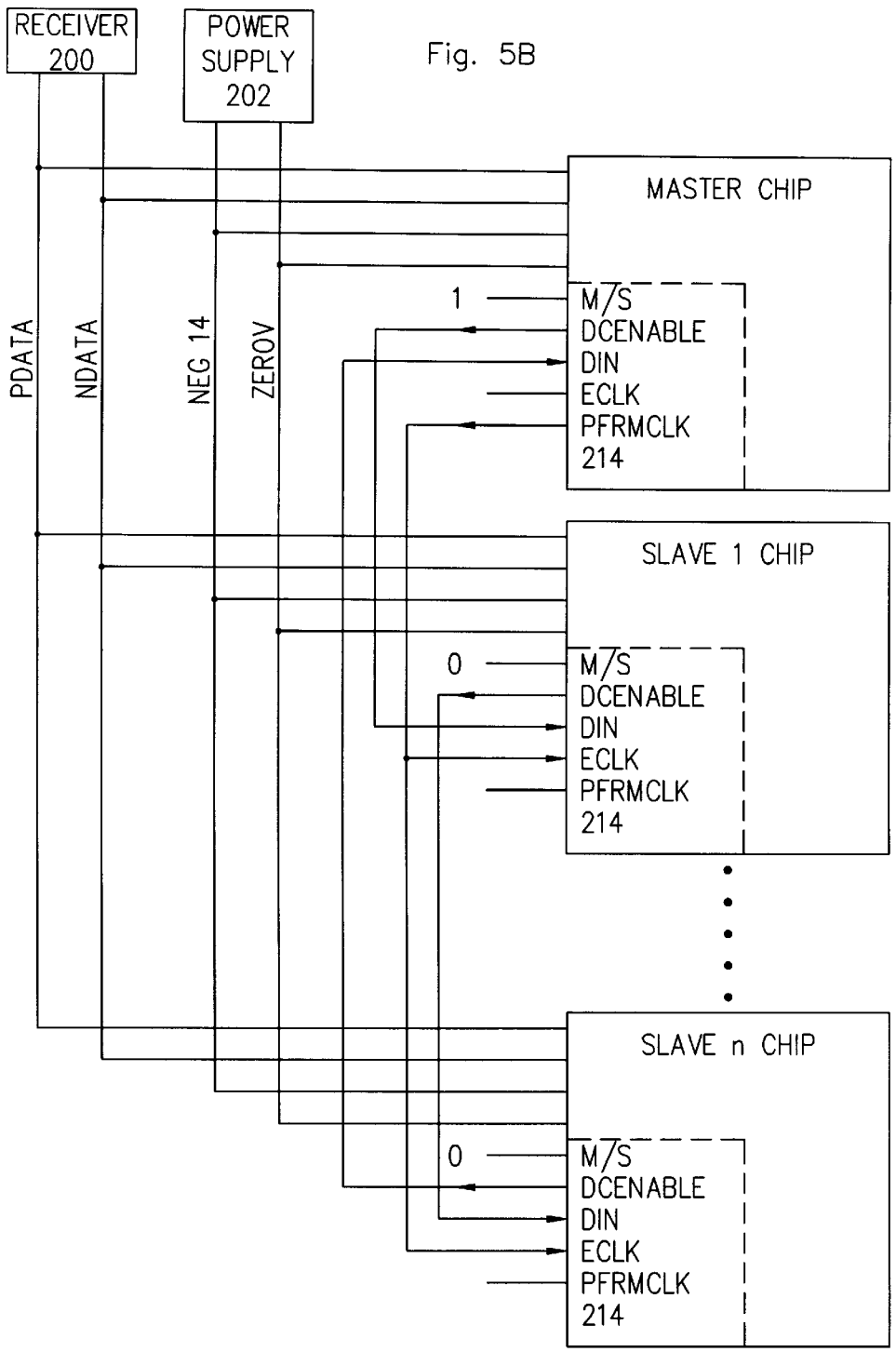
FIG. 5B is a block diagram of multiple chip system for the ICS of FIG. 2 or FIGS. 4A–4H.

An example of multiple chip system is set forth in FIG. 5B having a master chip and n slave chips. Each chip includes a multiple chip control circuit (214, 214-S1 to 214-Sn). As shown in FIG. 4E, chip control 214 has inputs PFRMCLK from the clock decoder 201B, RFMAIN from refresh voltage logic 210, PFMAIN from the pulse width control 209, a preset master/slave input M/S ("1" for the master chip and "0" for all slave chips) and open input leads DIN and ECLK. The control 214 outputs going off-chip include PFRMCLK (for connection to each of the inputs ECLK of the slave chips) and DCENABLE (for a control signal applied to the serial to parallel converter 201C). The chip control 214 in each slave chip includes the same input and output lines. However, each line ECLK is connected to receive the signal PFRMCLK from the master chip, each line PFRMCLK is open and each line DIN is connected to DCENABLE of the preceding chip.

Basically each chip control includes a conventional gate flip-flop. In the chip control 214, the gated flip-flop is preset by M/S=1 and changes state to develop the control signal DCENABLE upon receipt of PFRMCLK (indicative of the long frame marker when in multiple mode operation and indicative of standard end of frame pulse during regular single chip operation). As previously discussed, DCENABLE enables operation of 201C to develop DATA (1–9) from MANDATA and hence the processing of input data from the WP by the ICS. In multiple chip operation, as depicted in FIG. 5B, DCENABLE from chip control 214 is applied to input DIN of chip control 214-S1. This effects a preset of the flip-flop in 214-S1, which will change state to develop a control signal DCENABLE for output to the chip control 214-S2 at its DIN input upon receipt of the next PFRMCLK at the ECLK input of 214-S1. DCENABLE developed within 214-S1 is applied to the serial to parallel converter 201C in the ICS of the Slave 1 chip to enable processing of data from the WP by that ICS. This process is repeated in sequence for each slave chip. From slave n chip, DCENABLE is fed back to the DIN input of the master chip to complete the ring.

Thus, in the multiple chip operation, the flip-flops in each chip control are ganged together such that the output DCENABLE of the master chip feeds into the DIN input of the next slave flip-flop and the DCENABLE output of the next slave chip feeds into the DIN input of the following slave flip-flop and so on until the DCENABLE of the last chip feeds into DIN input of the master chip flip-flop. In this way, the flip-flops form a ring-type shift register.

The multiple chip operation also allows for short frames and short-long frames. With an early application of a long frame pulse or marker, the long frame can be shortened. Further, when WORD9 commands requiring more than one frame for loading and execution are in process, the frame pulse may be inhibited as a clock pulse for the flip-flops until the WORD9 command is fully executed.

Having described each section and subsection of the ICS of FIG. 4, the following is a description of the general operation of the ICS.

System Operation (a) Power Supply

The ICS has no internal power source and, therefore, is completely dependent for power from an outside source, that is, power radiated by the antenna connected to the wearable processor WP. The magnetic portion of that radiated field is received by the ICS and converted into two types of signals. One is the power supply for the balance of the implantable system and the second is the data stream which contains the commands which control the behavior of the ICS. The data stream coming from WP is a 50% duty cycle amplitude-modulated signal. The modulated carrier is converted to RAWDC power in receiver 200. The DC power, RAWDC, is passed to series regulator 202A and its associated circuitry to generate a regulated negative 14 volts, NEG14, which is the primary power supply for the ICS. The primary power is further operated on to create various voltage levels for the balance of the circuitry. The principal derived power supply is the output from the downconverter 203B, which is the −3.5 volt line, used to power much of the logic circuitry within the ICS. Also derived are −7 volts, −10.5 volts, and the original −14 volts, which are supplied to the output circuits, of which there are 8. Each output circuit utilizes one of 4 different levels of refresh voltages, which can be selected according to requirements for stimulation output of a given channel in the ICS. In addition, the −14 volt supply is used to power much of the ICS analog circuitry to provide rail to rail operation, where the rails are defined by the −14V line and the ZEROV line. ZEROV is common to all the circuitry, except for the isolated output stages, and is the logic true or logic one level for all the logic circuitry. The zero or false logic level is −3.5V or −14V, depending on the power supply for a particular logic section.

The signals TANKV from receiver 200 and TAP14 from regulator 202A are resistively-divided representations of RAWDC and NEG14, respectively. As indicated at telemetry MUX 211B, TANKV and TAP14 are applied to the back telemetry system so that closed loop control of the incoming DC power to the ICS can be maintained. In particular, during startup, the microprocessor in the WP sets the transmit power to a level sufficient to insure proper operation of the ICS (see FIG. 1 and related text). Then, during operation of the ICS, TANKV and TAP14 are telemetered back to the WP for processing. Depending upon the magnitude of the difference between TANKV and TAP14, that is the voltage drop across the series regulator 202A, the transmit power of WP can be reduced by operation of the microprocessor. Preferably, the power transmitted to the ICS is just sufficient for normal operation, thereby conserving power drawn from the WP and its batteries.

(b) Initialization

As previously described, the WP startup procedure comprises transmission of a data stream of alternating ones and zeros. Simultaneously, the series regulator 202A output NEG14 ramps from 0 to −14 volts with respect to ZEROV and the receiver develops outputs PDATA and NDATA at half the standard bit transmission rate (550 KHz) to data conditioner 201A. Within 201A, PDATA and NDATA result in the signal MANDATA which is transmitted to downconverter clock 203A, clock decoder 201B and serial to parallel converter 201C. Within downconverter clock 203A, MANDATA is divided by four in passing through two toggle flip-flops. The resulting 137.5 KHz signal is applied to one input to a two-pole FET selector switch, the other input comprising WORDTRCLK from serial to parallel converter 201C. The state of the switch is controlled by POWERBAD, which is asserted during system startup to cause the switch to transmit the 137.5 KHz signal. Thus the 137.5 KHz signal is selected as the clock signal for the voltage downconverter 203B during startup operation of the ICS whereas a level-shifted version (−3.5 to −14V) of WORDTRCLK (122 KHz) from converter 201C is selected during normal operation of the ICS (DOWNCLOCK).

Also during initial startup, the powerbad detector 204A asserts POWERBAD from just after the start of transmission until the −3.5 volt power supply reaches about −3.3 volts. As previously described, POWERBAD drives the reset of logic circuitry in many parts of the ICS and also forces the output stages 212 to be off so that no stimulus can be presented until proper functioning of the ICS is determined. This is accomplished by POWERBAD resetting a flip-flop within 204B to OUTENABLE, the assertion of which is required to enable the output stages 212. Then, upon a negation of POWERBAD, assertion of CARDET from clock decoder 201B and assertion of CONNECT and PLLLOCK from command decoder 206B, the flip-flop is set and OUTENABLE is asserted to enable the output stages 212. Similarly, the assertion of PALARM from parity error detector 204C results in a disabling of the output stages 212 via a negation of OUTENABLE.

In addition, during power-up of the ICS, the carrier of the back telemetry transmitter section 211 is turned on and the turning on of that carrier is sensed by the WP and indicates normal operation of the ICS. Such turning on of the carrier is accomplished by assertion of CARON from 204B. As previously described, CARON is generated only when signals CARDET and PLLLOCK asserted and signal POWERBAD and PALARM not asserted are combined in gates in 204B to indicate proper operation of the ICS. From 204B, CARON goes off chip to turn on the back telemetry carrier signal at a telemetry transmitter 211E of the back telemetry section 211, the back telemetry section being off-chip. If at any time any of the signals CARDET, PLLLOCK, POWERBAD or PALARM changes to a different state indicative of a problem condition, CARON will be negated and the back telemetry carrier will be turned off. Thus, if at any time the WP no longer detects the back telemetry carrier from the ICS, we assume that improper operation is in progress. The microprocessor in the WP halts data transmission and begins the above described startup procedure which should then result in detection of the back telemetry carrier from the ICS.

Following this initial handshake between the WP and the ICS, a series of patient-specific parameters which have been embedded in the WP via a clinician's programmer will be sent into the ICS. Once all such parameters are set up, the electrode outputs will be connected and stimulation will commence. This is accomplished via a WORD9 command to assert the command line CONNECT from the command decoder 206B followed by assertion of the OUTENABLE line from the initialization section, 204B. Assertion of OUTENABLE will enable an output from Pulse Width Control 209 [PWC (1–8)] which in matrix 212C will connect the electrode outputs (see table 6 herein). Conversely, the WP can force a global disconnect of all of the outputs at any time by sending in the WORD9 command which asserts the command line DISCON from the command decoder 206B. Of course, in the event of catastrophic failure of the stimulation circuitry, the user can disable the ICS simply by moving the headpiece away from the ICS.

If a parity error is detected by the parity error detector 204C the detector asserts line PALARM to the initialization section 204. Section 204 then issues the system reset signal SYSRESET to force the ICS system into its restart condition and turn off the back telemetry carrier, signaling the WP that a serious error has occurred. A new startup sequence will then ensue under control of the startup procedure of the WP.

(c) Data Recovery

The pair of data signals, PDATA and NDATA, coming from receiver 200 are squared up in the data conditioner 201A to generate the signal MANDATA. The signal MANDATA represents the recovered data signal from the Manchester-encoded stream transmitted by the WP to the ICS and, therefore, represents the primary data signal input into the ICS to control its function. In addition, the presence of modulated carrier is used to create the carrier detect signal CARDET. CARDET is connected to the clock decoder 201B to indicate the presence of carrier and therefore is one of the requisites for normal operation of the ICS. Since MANDATA is a Manchester-encoded signal, it comprises a clock and data. The clock information is extracted from MANDATA in the clock decoder 201B. The clock information is then expressed as 2 signals: CLKPH1 and CLKPH2, used to control the clocking of the serial data into a register in serial to parallel converter 201C. In the converter 201C the nature of the signal is converted from serial to parallel.

As previously discussed, data sent to the ICS by the WP is in the form of a serial bit stream organized within a frame, which consists of 9, 9 bit words, that is 81 bits, plus a parity bit and a frame-ending marker. The 9 bit data words, which make up the data portion of the frame, comprise 8 amplitude and polarity data words for the eight output channels in sequence 1 through 8, and a 9th word containing special commands which control housekeeping and certain other functions of the ICS.

In clock decoder 201B, the signal PFRMCLK is derived from the frame ending pulse. PFRMCLK signals the end of one data frame and, therefore, the beginning of the next.

In the converter 201C, WORDTRCLK is generated at the end of each 9 bit word transmitted and causes those specific 9 bits, DATA (1–9), to be latched into the amplitude data latch 205A for amplitude and polarity control. The signal WORD9CLK is used to cause latching of the 9th word coming in so that those 9 bits are directed to the command latch 206A and will remain in that latch until the next 9th word time. Thus, the amplitude data latch 205A is updated 8 times during the normal frame, with data for any particular channel being available only for the transmit time of the next word, when it is then replaced by the new data.

On the other hand, command latch 206A retains the 9th word command information for at least one complete frame time, that is, until the next 9th word occurs. Of course, the succeeding 9th word command could be the same command sent again, in which case the functionality requested by that command would simply be maintained for another frame or, potentially for additional frames for an unlimited period of time.

Note that at times when use of the 9th word command is not required, the frame can be shortened by sending the frame-ending marker after any word of the amplitude data information. The sequence of the data is amplitude and polarity data for channel 1, followed by 2 through 8, and this sequence can be terminated at the end of any word by a frame ending marker. This manner of operation is known as short cycling, and allows the frame to be shortened for more rapid update of low number channels but, of course, without 9th word commands. Such short cycle operation will allow higher frequency waveforms to be represented on such low-order channels at the expense of less-frequent updates on the higher order channels and the absence of 9th word command information. Under short cycling conditions, the amplitude and polarity information for channels not addressed, as well as 9th word commands not overwritten, will simply-maintain their previous setting until written again at some future time.

(d) Amplitude and Polarity Control

In the normal full frame sequence, amplitude and polarity data, that is 9 binary bits each for 8 different channels, is received in sequence for channels 1 through 8. The first amplitude and polarity data word received is latched as noted above, and then presented to the logarithmic D to A converter 207B during the second word transmit time. Thus, the update of amplitude and polarity information for a given channel lags that channel's transmit time by one word time. In addition, since the data queue is only one word deep, the amplitude and polarity information sent, for example for channel 1, has to be operated on and completed during the channel 2 transmit time. During that time, the logarithmic D to A converter 207B uses the 8 bits of amplitude information to operate on the reference current IREF from the current reference generator 207A to generate the two current control voltages IPOSCON and INEGCON, which are passed to the analog multiplexer 207C as signals IPOS and INEG. IPOS and INEG are the gate-to-source voltage which will be impressed on the current source 212B in the appropriate output signal channel under the control of the signal WSTRB appropriate for that particular channel. The signals WSTRB (1–8) arise from the word strobe generator 201D, and are a sequence of pulses which are active in the appropriate word time for each channel in sequence 1 through 8. The current source 212B in each of the 8 individual isolated output channels, stores its appropriate gate-to-source voltage on capacitance associated with the MOSFET, maintaining control at the commanded level until updated in the next frame. Each of the 8 current sources is a unidirectional current-controlling device which controls output current drawn from the refresh voltage capacitorlabeled CRV in FIG. 4.

Each current source 212B is only connected to the logic circuitry during its signal transfer time. The refresh voltage capacitor CRV1 is only connected during its transfer time. Thus, for the balance of the time of operation, each output channel is electrically isolated from all other channels and also from the logic circuitry.

Since the MOSFET comprising current source 212B is unidirectional, the switching network 212C is placed after the current source in order to control the direction of stimulus current. This aspect is controlled by the signal POLARITY from latch 205A, which for bipolar operation directs the electrode switching matrix 212C to connect output A1 and output B1 for the first channel, for example, directly to the lines +IN1 and −IN1 for normal polarity, or to −IN1 and +IN1 for reverse polarity. In this way the direction of current flow between the electrodes can be controlled to be in either direction, even though the actual current source is a unidirectional device. For monopolar operation, as opposed to bipolar operation as described above, the electrode switching matrix 212C, along with the indifferent electrode switch 212D, is configured to allow the output to be generated between output A1 and the indifferent electrode or output B1 and the indifferent electrode with either direction of current flow being possible. The selection of bipolar or monopolar style of output in the matrix 212C is under control of the buses AMONO (1–8) and BMONO (1–8) from output mode register 208. In this regard, AMONO (1–8) and BMONO (1–8) each have one representative line going to each of the eight output channels (see Table 6).

In addition, there is a capability for placing a discharge resistor across each pair of outputs. Such function is under control of the discharge resistor control bus lines DRC1–8. Assertion of a DRC line to a particular output by the output mode register 208 will place a 150K resistance across the output terminals to discharge the output coupling capacitors. Alternatively, or in addition, a low resistance connection in 212C can be placed across the output terminals to more rapidly discharge the output coupling capacitors in response to the signal SHORT from the zero current control 205B. Further, the output current can be forced to zero by assertion of the signal ZERO from zero current control 205B. In this regard, the signal ZERO causes all output switches in the switching matrix 212C to be in an off or high impedance state.

An additional output mode (MULTIPOLAR MODE) involves using a pair of output channels to generate a bipolar output using any pair of electrodes in the electrode array. To accomplish this, two channels are programmed by the output mode register 208 to assume a monopolar mode. This causes one side of each of the selected channels to be connected together and to the indifferent electrode. Then, unlike the normal monopolar mode, a WORD9 command from WP is sent to the ICS to disconnect the indifferent electrode via IECLOSE. Thus, by programming one of the channels as a source and the other as a sink, current can be driven through any selected pair of electrodes with complete control over amplitude and polarity.

(e) Pulse Width Control

The amplitude and polarity control described above is typical of the analog operation of the ICS. An additional mode of operation is provided by the ICS in which the described amplitude and polarity control is still in operation, but the outputs to one or more channels, controlled individually, can be turned on and off in order to create pulses of controlled amplitude and controlled duration. This is the pulsatile mode of operation. Pulsatile operation is under the control of pulse width control 209. Pulse width control is via a sequence of 9th word commands (WORD9), the first of which results in the assertion of the line FUNC8 which enables the pulse width control 209. The first such command also contains information about the placement of pulse edges within the next succeeding frame, and the rest of the command is issued in a series of 9th words which must not be interrupted by any other 9th word command. Therefore, a feedback signal to prevent other 9th word commands from interfering is sent back from the pulse width control 209 to the command decoder 206, that signal being PFMAIN.

In the control 209, bits of the first of the pulse width commands and succeeding ones are loaded into the pulse width control registers. The bits are used to preset downcounters, driven by the internal system clock, to control the appearance of the on and off times for the channel which is being controlled. Therefore, on a channel by channel basis, the amplitude of the pulse can be controlled in the usual way by the amplitude and polarity information sent in for that channel, and the turning on and off of the output is controlled by the pulse width control 209 in conjunction with the electrode switching matrix.

In addition to the channel by channel control of outputs being either on or off via the pulse width control 209, there is also a global control which can enable or disable all outputs from all channels simultaneously, that is via the signal OUTENABLE from the initialization section 204B. The global signal OUTENABLE can be controlled by the outputs, CONNECT and DISCON, from the command decoder 206B. That is, the line can be driven by a 9th word command to connect or disconnect all the outputs. In addition, the global output control, OUTENABLE, can be negated by the initialization section 204B when circuitry in that section detects conditions of improper operation. Furthermore, during startup of the ICS, all outputs are disconnected until normal operation is in progress, at which time OUTENABLE is asserted and stimulation will begin.

(f) Refresh Voltage Control

The isolated power supply voltages for the stimulus currents from each of the 8 output channels is provided by charge stored on the refresh capacitors, CRV1 through 8. Selection of the appropriate voltage level for each of the 8 output stages is a decision made by the WP based on information telemetered back to it from the ICS about the voltage requirements for proper output drive of that individual channel. This is an important power conservation feature of the ICS which seeks to minimize the potential difference and, therefore, the power dissipation in the current source 212B.

Any one of four different power supply voltage levels are selectable for each of the output channels, independently, and those voltages are −3.5, −7.0, −10.5, and −14. Refresh voltage control on a channel by channel basis is effected by two sequential 9th word commands which are decoded in the command decoder 206B and result in assertion of the signal FUNC7 line going to refresh voltage logic 210. This requires 2 full frames to implement, that is two 9th words must be transmitted in sequence to achieve such control. The command decoder 206B must be prevented from operating on a different 9th word during the sequence, hence the line RFMAIN from refresh voltage logic 210 is applied to the command decoder to lock it into the refresh voltage sequence for two frames. Refresh voltage logic 210 provides 2 bits RV0 and RV1 which define the four possible power supply voltage levels for each of the 8 output channels via the lines RV0 (1 to 8) and RV1 (1 to 8) connected to refresh voltage control 212A. The control bits, two for each channel, are latched into their respective refresh voltage control so that (1) one of the four possible power supply voltage levels is selected for each associated channel, e.g., −3.5 for channel 1, −10.5 for channel 2, −14 for channel 3, −7 for channel 4, and so on, and (2) the selected power supply levels are maintained until changed by a new refresh voltage command. During startup, all 8 output channels are automatically commanded to use the −14 volt refresh, which provides for the maximum output power. As the system continues to run and, as described hereinafter at (g) "Back Telemetry", as information is fed back via telemetry to the WP, logic within the microprocessor of the WP can then cause a reduction in the power supply voltage for each channel to a level most appropriate for the stimulation requirements for that channel, thereby enhancing the power conservation within the ICS.

(a) Back Telemetry

Function codes FUNC4 and FUNC5 from the command decoder 206B enable the function of the back telemetry section 211 which is to report back to the WP the state of various voltages within the ICS. As previously indicated, some of the functions of the telemetry section are of a housekeeping nature. For example, the measurement and transmission back of the voltage TANKV provides an index or status indication of the RAWDC voltage generated in the ICS in response to data from the WP. In addition, the power supply voltages ZEROV, −3.5 volts and TAP14 are available for transmission back to the WP as indicators of proper power supply function and for feedback control of the WP and the power transmitted therefrom to the ICS.

Also, the back telemetry can be commanded to measure and send back the value of the voltage reference, VREF, to indicate proper operation and, since this voltage is highly stabilized, to provide a system calibration point. In addition, stimulus output voltages can be measured via the lines OUTA (1 through 8), and OUTB (1 though 8), when the ICS is in the bipolar mode.

In the monopolar mode, the output voltage can be measured between either output A and the indifferent electrode, or output B and the indifferent electrode, whichever is appropriate. Additionally, in the monopolar mode, the current sampling resistors RLO or RHI can be placed in series with the stimulus circuit, and the resulting voltage drop across the resistors measured and transmitted back to the WP as an index of stimulus current. Thus, in the monopolar mode, both the stimulus voltage and current can be measured and, thereby, the impedance of the electrode and the tissue-electrode interface can be measured and transmitted back to the WP. The WP is able to use this information in its microprocessor to choose the appropriate refresh voltage for each channel in the manner heretofore described at (f) Refresh Voltage Control.

As indicated in FIG. 4, following the telemetry multiplexer 211B which selects the signal to be measured and transmitted back to the WP, inputs are generated for the analog to digital converter section 211C. The analog to digital converter is of a unipolar type. But, at least some of the signals which are to be measured have unknown polarity at the time of measurement. Therefore, the capability is provided to make measurements in a normal mode or an inverted mode, depending on the state of the function lines, FUNC4 and FUNC5. If FUNC4 is asserted at the converter 211C and the resulting ADCOUNT is zero, this indicates either that the measured signal is zero or of a polarity opposite to the setting of the converter. To determine which is the case, FUNC5 is asserted to switch the converter to the inverted mode. If ADCOUNT now registers other than zero, this indicates that the measured signal was of an opposite polarity to the normal setting of the converter. If ADCOUNT remains zero, this indicates that the measured signal was in fact zero.

In addition, the amplitude of some of the voltages to be measured is unknown at the time of measurement. Therefore provision is made for a stepwise gain selection prior to analog to digital conversion under control of SH2X1, SH2X3, SH2X10 and SH1X10. For example, if SH2X1 is asserted and ADCOUNT is a series of 1's, the input is out of range of the converter and the gain should be reduced until ADCOUNT reads less than 111111.

Thus, if the measurement is taken and is judged by the WP to be of the wrong polarity or wrong gain setting, correction can be sent back from the WP to make another measurement using the correct parameters as deduced from the first reading. The 6 bit parallel output bus from the A to D converter is connected to the telemetry modulator multiplexer which converts this parallel set of bits into a serial bit stream which is then applied to the back telemetry transmitter.

Physician's Tester

As described herein most clearly under the heading "SYSTEM OPERATION", the system of the present invention provides for feedback and microprocessor control of various power levels and measurement of different voltages and currents within the ICS in response to commands and data changes transmitted by the WP in response to data telemetered back to the WP in the form of status indicating and measurement signals. The present invention also contemplates physician control over the selection of voltages and currents to be measured and the presetting of parameters in the ICS during testing of the ICS and/or a patient's response to data transmitted by the WP to the ICS.

Figure 6:
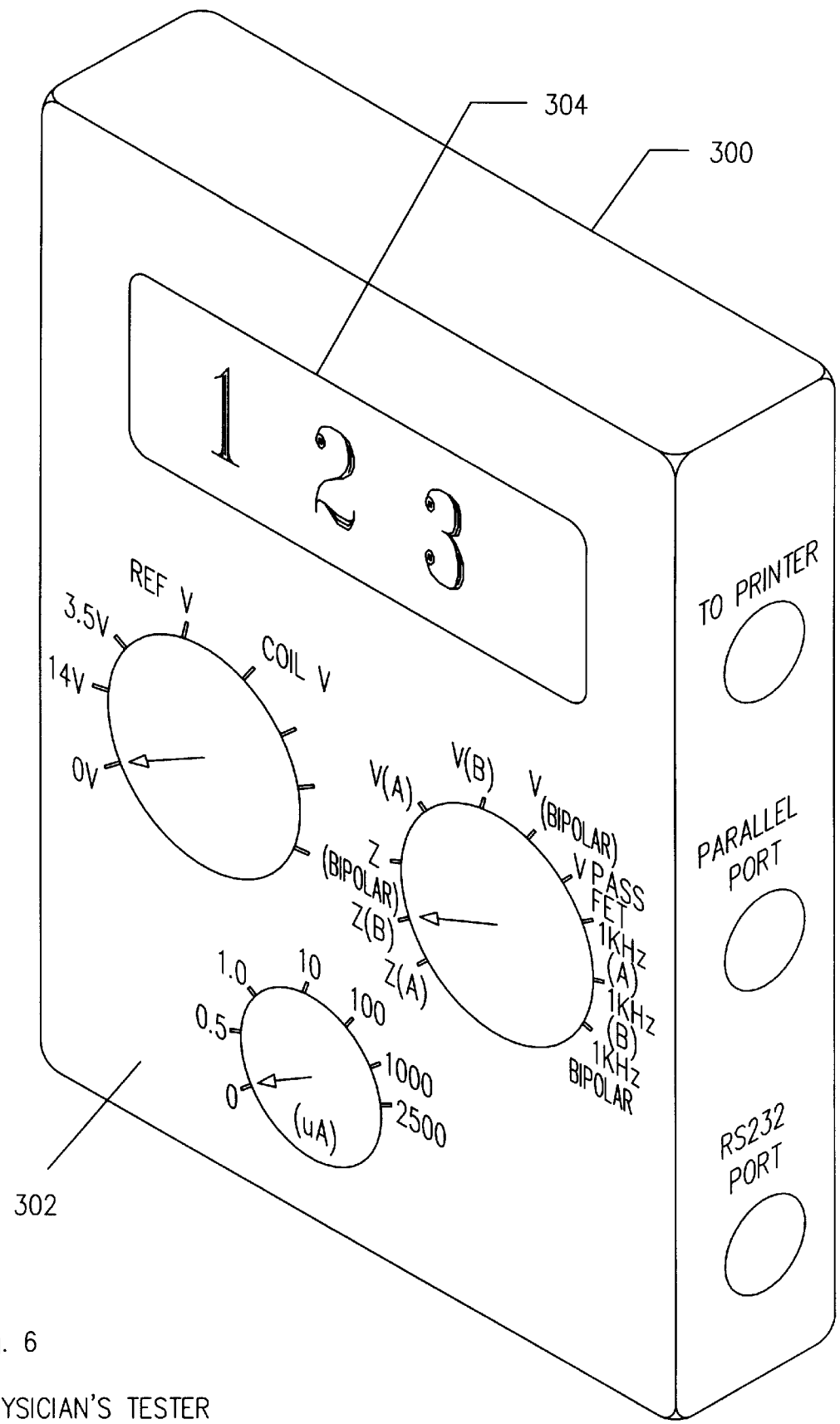
FIG. 6 is a diagrammatic representation of a physician's tester useful with the cochlear system of FIG. 1.
Figure 7:
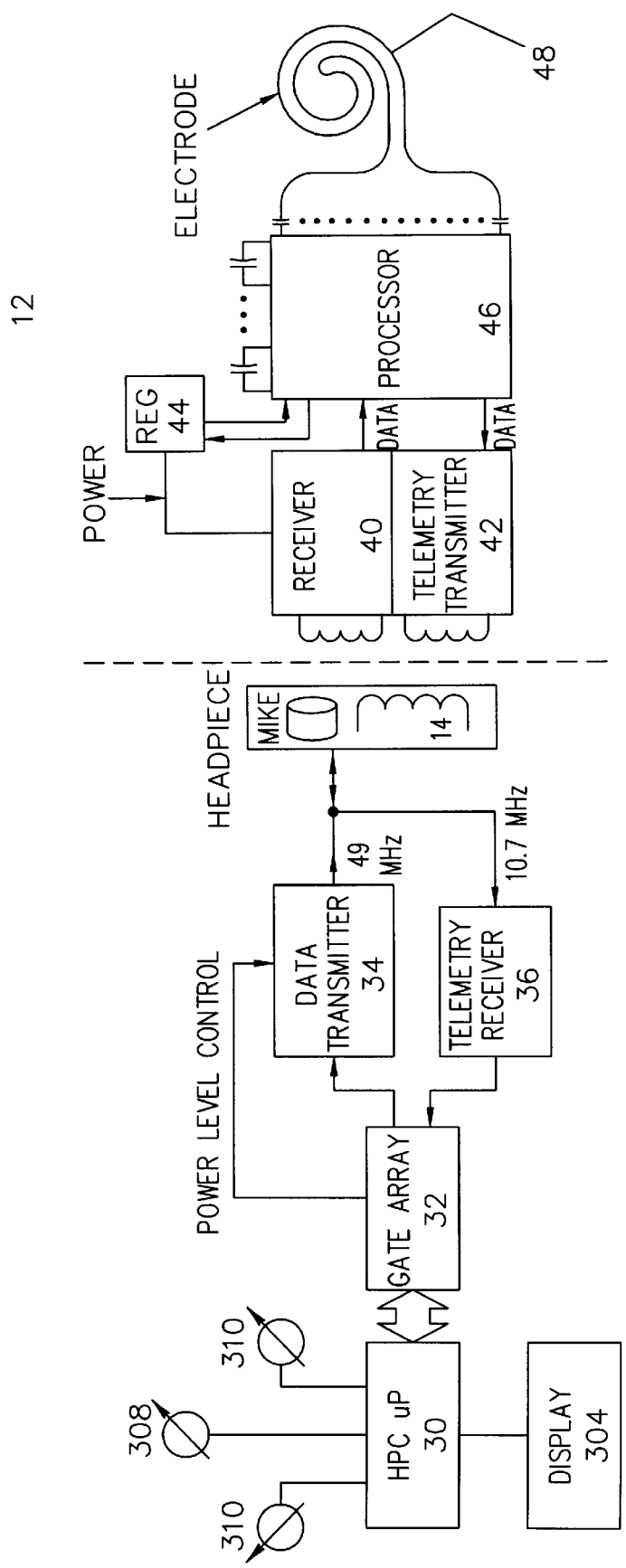
FIG. 7 is a block diagram of the cochlear system of FIG. 1 with the WP replaced by the physician's tester.

Basically such physician control is embodied in a portable tester utilizing telemetry coupling to the implanted ICS, thereby providing communication between the tester and ICS for the monitoring, control and measurement of the ICS parameters. In this regard, the tester as shown in FIG. 6 comprises a modification of the previously described WP embodied in a portable housing 300 having a control panel 302 and a visual display 304 providing alpha numeric data for viewing and appropriate action by the physician. A block diagram of the circuitry embodied in the tester is depicted in FIG. 7 in combination with the ICS 12 of FIG. 1—all previously described components bearing the same numerals as in FIG. 1.

The tester monitors the performance parameters of the ICS 12 by detecting the back telemetry signal of the ICS in an interrogation protocol for the microprocessor. The tester places the received signal into a self contained memory storage section.

Physician interaction with the ICS is exercised by the use of the control panel 302 which contains electronic circuitry for conversion of the back telemetry signal into directly readable information which is read out on the LCD display 304. Commands are provided to the implanted stimulator through a control of the microprocessor 30 and the commands generated thereby. The physician's tester additionally can provide a print out of both the displayed data and information and the executed commands.

As illustrated, the physician's tester is basically a modification of the WP 16. The Physician's Tester microprocessor 30 has both a display port and an infrared serial output port. The display port drives display 304 while the infrared port can drive a separate infrared display, a printer for recording the displayed information or a separate IR transducer for generating infrared light signals for transmission to an IR receiver for separate processing of the information from the ICS. Panel knob 306, 308, and 310 control potentiometers, the position of which are read by the microprocessor 30 to control the commands generated thereby and hence the parameters measured and displayed by the ICS and Physician's Tester combination. In particular, such manual control results in changes in the commands transmitted by the WP to the ICS to control the measurement of the ICS parameters in the same manner as previously described for the system of FIG. 4.

Table 7 describes typical parameter settings for the control knobs 306, 308, and 310.

TABLE 7

| Control Knob 306 | | |
|---|---|---|
| Position 1 | = | Ground (0 Volts) |
| Position 2 | = | 14.0 Volts |
| Position 3 | = | 3.5 Volts |
| Position 4 | = | Reference Voltage |
| Position 5 | = | Coil Voltage |
| Control Knob 308 | | |
| Position 1 | = | Impedance of Monopolar A configured channel |
| Position 2 | = | Impedance of Monopolar B configured channel |
| Position 3 | = | Impedance of Bipolar configured channel |
| Position 4 | = | Voltage of Monopolar A configured channel |
| Position 5 | = | Voltage of Monopolar B configured channel |
| Position 6 | = | Voltage of Bipolar configured channel |
| Position 7 | = | Voltage of Pass FET |
| Position 8 | = | 1 KHz output current Monopolar A configured channel |
| Position 9 | = | 1 KHz output current Monopolar B configured channel |
| Position 10 | = | 1 KHz output current Bipolar configured channel |
| Control Knob 310 | | |
| Volume Control (Peak Output Current) | | |
| Position 1 | = | 0 $\mu$A |
| Position 2 | = | 0.5 $\mu$A |
| Position 3 | = | 1.0 $\mu$A |
| Position 4 | = | 10 $\mu$A |
| Position 5 | = | 100 $\mu$A |
| Position 6 | = | 1000 $\mu$A |
| Position 7 | = | 2500 $\mu$A |

Extended System Operation and Applications

While preferred forms of the human tissue stimulator of the present invention embodied in cochlear stimulating systems have been described in detail hereinabove, it should be appreciated that various changes and modifications may be made in the described systems without departing from the spirit of the present invention.

For example, while the outputs of the preferred embodiments have been described as stimulating tissue, the DC and squarewave outputs of the ICS under control of the pulse width control 209 may be utilized to power other implanted devices. For some such AC applications, a larger capacitor CA1 and/or CB1 may be required for each or some of the ICS output channels. Conversely, for strictly DC applications, no output capacitors are necessary.

Further, while the ICS status signal-generating features for the preferred embodiment include the measurement and telemetry functions described in subsection (g) hereinabove, similar measurements and telemetry back to the WP may be provided by the ICS for other implanted devices connected to an electrode pair of the ICS. This permits a wide range of applications since the back telemetry feature can sample and measure any external voltage within its amplitude and frequency range and provide 6 bit resolution. Any external device which can generate an appropriate voltage related to its function can utilize this feature.

Moreover, with the ICS as previously described with respect to FIG. 4, the output electrode pairs for the separate channels of the ICS are simultaneously available to power another implanted device or stimulate tissue and to sense variable voltage conditions therebetween.

In view of the foregoing and other additions and changes which may be made in the illustrated embodiments, the present invention is to be limited in scope only by the terms of the following claims.

We claim:

1. A cochlea stimulation system, comprising:
   audio signal receiving means, including a headpiece coupled to a signal and energy coupling means, the headpiece having transmitting and receiving means and means for transferring data through the signal and energy coupling means at one frequency for data that originates from an implanted cochlea stimulator (ICS) and is sent to an externally wearable signal processor (WP); and at another frequency data and energy originate from the WP and are sent to the ICS;
   said WP receives and processes audio signals received by the audio signal receiving means and includes means for generating data indicative of the audio signal;
   means for transmitting the data to the ICS, the ICS including:
      means for receiving transmissions from the WP,
      processor means for processing such transmissions to generate stimulation signals,
      a plurality of electrically isolated capacitor-coupled cochlea stimulating electrodes for receiving the stimulation signals,
      means in the ICS responsive to data from the WP for selectively monitoring at least one of the electrodes or voltages in the processor and for generating ICS status indicating signals,
      means in the ICS for transmitting such ICS status indicating signals to the WP; and
   means in the WP for receiving and processing the ICS status indicating signals.

2. The system of claim 1 wherein the means in the headpiece comprises tuned inductive capacitive filters.

3. The system of claim 1 including means for electrostatically shielding the coils in the headpiece and ICS so that only magnetic coupling occurs.

4. The system of claim 1 wherein stimulation signals are pulses and further including means in the processor for selectively controlling the pulse width of the stimulation signals.

5. The system of claim 1 further including means in the processor for selectively controlling the frequency at which stimulating signals are applied to selected ones of the electrodes.

6. A cochlea stimulation system, comprising:
   audio signal receiving means;
   an externally wearable signal processor (WP) for receiving and processing the audio signals received by the audio signal receiving means and including means for generating data indicative of the audio signal;
   means for transmitting the data to an implanted cochlea stimulator (ICS), the ICS including:
      means for receiving transmissions from the WP,
      processor means for processing such transmissions to generate stimulation pulses and for controlling the pulse width of the stimulation pulses,
      a plurality of electrically isolated capacitor-coupled cochlea stimulating electrodes for receiving the stimulation pulses,
      means in the ICS responsive to data from the WP for selectively monitoring at least one of the electrodes or voltages in the ICS and for generating ICS-status-indicating signals, and means in the ICS for transmitting such ICS-status-indicating signals to the WP; and means in the WP for receiving and processing the ICS-status-indicating signals.

7. The system of claim 6 further including means for transmitting power signals from the WP to the ICS, means in the ICS for processing the power signals and for generating power for the ICS, and means in the WP responsive to at least a portion of the status indicating signals for controlling the power level of transmissions to the ICS.

8. The system of claim 7 further including means in the ICS and responsive to the power signals for generating a plurality of voltages for powering different components in the ICS.

9. A cochlea stimulation system, comprising:

audio signal receiving means;

an externally wearable signal processor (WP) for receiving and processing the audio signals received by the audio signal receiving means and including means for generating data indicative of the audio signal;

means for transmitting the data to an implanted cochlea stimulator (ICS), the ICS including:
 means for receiving transmissions from the WP,
 a processor for processing such transmissions to generate stimulation signals,
 a plurality of electrically isolated capacitor-coupled cochlea stimulating electrodes for receiving the stimulation signals,
 means for selectively controlling the frequency at which stimulating signals are applied to selected ones of the electrodes,
 means responsive to data from the WP for selectively monitoring at least one of the electrodes or voltages in the ICS and for generating ICS-status-indicating signals,
 means for transmitting such ICS-status-indicating signals to the WP; and means in the WP for receiving and processing the ICS-status-indicating signals.

10. The system of claim 9 further including means for isolating electrical signals on any pair of electrodes independent of electrical signals on any other pair of electrodes.

11. The system of claim 9 further including in the ICS means for selectively generating analog and pulsatile stimulating signals.

12. The system of claim 9 further including in the ICS means for selectively stimulating the electrodes as either unipolar or bipolar electrodes.

13. The system of claim 9 further including means for powering down the ICS when audio signals are not received by the WP and for rapidly powering up the ICS in response to the reception of audio signals at the WP.

14. A cochlea stimulation system, comprising:

audio signal receiving means;

an externally wearable signal processor (WP) for receiving and processing the audio signals received by the audio signal receiving means and including means for generating data indicative of the audio signal;

means for transmitting the data to an implanted cochlea stimulator (ICS), the ICS including:
 means for receiving transmissions from the WP,
 processor means for processing such transmissions to generate stimulation signals,
 a plurality of electrically isolated capacitor-coupled cochlea stimulating electrodes for receiving the stimulation signals,
 means responsive to data from the WP for selectively monitoring at least one of the electrodes or voltages in the ICS and for generating ICS-status-indicating signals therefrom, and
 means for transmitting such ICS status indicating signals to the WP;

means in the WP for receiving and processing the ICS status indicating signals;

means for transmitting power signals from the WP to the ICS;

means in the ICS for processing the power signals and generating power for the processor; and means in the WP responsive to at least a portion of the status indicating signals for controlling the power level of transmissions to the ICS.

15. A cochlea stimulation system, comprising:

audio signal receiving means;

an externally wearable signal processor (WP) for receiving and processing the audio signals received by the audio signal receiving means and including means for generating data indicative of the audio signal;

means for transmitting the data to an implanted cochlea stimulator (ICS), the ICS including
 means for receiving transmissions from the WP,
 processor means for processing such transmissions to generate stimulation signals,
 a plurality of electrically isolated capacitor-coupled cochlea stimulating electrodes for receiving the stimulation signals,
 means responsive to data from the WP for selectively monitoring at least one of the electrodes or voltages in the processor and for generating ICS-status-indicating signals, and
 means for transmitting such ICS status indicating signals to the WP;

means in the WP for receiving and processing the ICS-status-indicating signals; and means for powering down the ICS when audio signals are not received by the WP and for rapidly powering up the ICS in response to the reception of audio signals at the WP.

* * * * *

US005938691C1

(12) EX PARTE REEXAMINATION CERTIFICATE (10472nd)

United States Patent
Schulman et al.

(10) Number: US 5,938,691 C1
(45) Certificate Issued: Jan. 13, 2015

(54) MULTICHANNEL IMPLANTABLE COCHLEAR STIMULATOR

(75) Inventors: Joseph H. Schulman, Santa Clarita, CA (US); John C. Gord, Venice, CA (US); Primoz Strojnik, Granada Hills, CA (US); David I. Whitmoyer, Los Angeles, CA (US); James H. Wolfe, Canyon County, CA (US)

(73) Assignee: Alfred E. Mann Foundation for Scientific Research, Sylmar, CA (US)

Reexamination Request:
No. 90/013,294, Jul. 9, 2014

Reexamination Certificate for:
Patent No.: 5,938,691
Issued: Aug. 17, 1999
Appl. No.: 09/103,264
Filed: Jun. 23, 1998

Related U.S. Application Data

(60) Division of application No. 08/450,041, filed on May 25, 1995, now Pat. No. 5,776,172, which is a continuation of application No. 08/322,065, filed on Oct. 12, 1994, now Pat. No. 5,531,774, which is a continuation-in-part of application No. 08/023,584, filed on Feb. 26, 1993, now Pat. No. 5,603,726, which is a continuation of application No. 07/752,069, filed on Aug. 29, 1991, now abandoned, which is a continuation-in-part of application No. 07/411,563, filed on Sep. 22, 1989, now abandoned.

(51) Int. Cl.
*A61N 1/36* (2006.01)
*A61F 2/18* (2006.01)
*H04R 25/00* (2006.01)

(52) U.S. Cl.
USPC .............................................. 607/57; 607/55

(58) Field of Classification Search
None
See application file for complete search history.

(56) References Cited

To view the complete listing of prior art documents cited during the proceeding for Reexamination Control Number 90/013,294, please refer to the USPTO's public Patent Application Information Retrieval (PAIR) system under the Display References tab.

*Primary Examiner* — Karin Reichle

(57) ABSTRACT

A cochlea stimulation system includes a patient wearable system comprising an externally wearable signal processor (WP) and a headpiece in electronic communication with an implanted cochlear stimulator (ICS). The ICS comprises eight output stages each having two electrically isolated capacitor-coupled electrodes, designated "A" and "B", circuits for monitoring the voltages on these electrodes, and circuits for both transmitting status information to and receiving control information from the WP. Based upon information received from the WP, a processor within the ICS can control both the frequency and the widths of the output stimulation pulses applied to the electrodes and may select which electrodes to monitor. The ICS receives power and data signals telemetrically through the skin from the WP. To save power, the ICS may be "powered down" by the WP based upon the absence of audio information or "powered up" if audio is present. The WP communicates with the headpiece over a co-axial cable using one frequency for transmitting signals and a second different frequency for receiving signals.

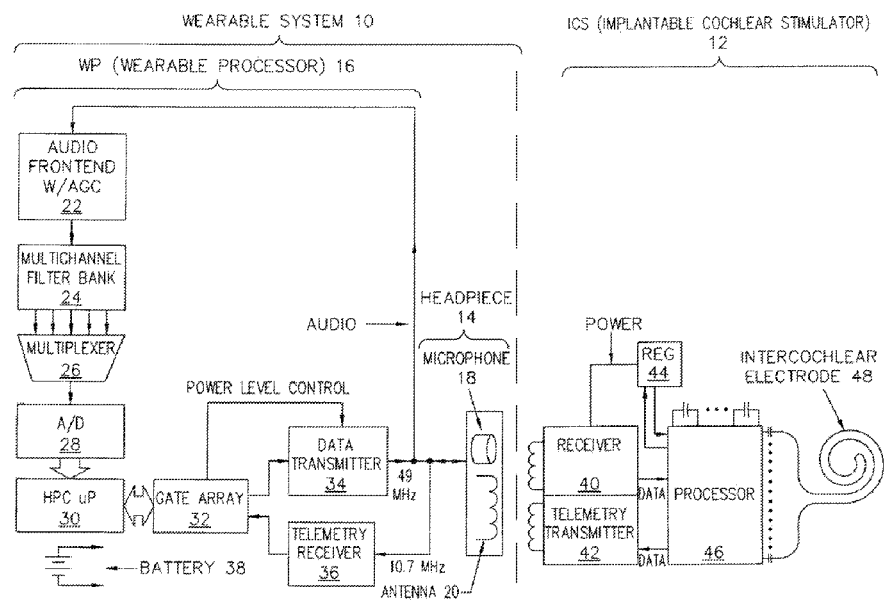

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 6-7 is confirmed.

Claims 1-5 and 8-15 were not reexamined.

* * * * *

(12) SUPPLEMENTAL EXAMINATION CERTIFICATE

United States Patent  
Schulman et al.

(10) Number: US 5,938,691 F1  
(45) Certificate Issued: Jul. 30, 2015

Control No.: 96/000,106  
Primary Examiner: Karin Reichle

Filing Date: May 12, 2015

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 4,532,930 A | 8/1985 | Crosby et al. |
| 4,612,934 A | 9/1986 | Borkan |
| 4,947,844 A | 8/1990 | McDermott |
| 3,906,166 A | 9/1975 | Cooper et al. |
| 4,524,774 A | 6/1985 | Hildebrandt |

FOREIGN PATENT DOCUMENTS

| | | |
|---|---|---|
| EP | 0259906 A2 | 3/1988 |

OTHER DOCUMENTS

Relevant Excerpts of the Report of Gerald E. Loeb, M.D., November 25, 2012, submitted in Alfred E. Mann Foundation v. Cochlear Corp., No. 2:07-cv-08108-FMO-SH (C.D. Cal.).

Relevant Excerpts of the Report of Gerald E. Loeb, M.D., January 19, 2009, submitted in Alfred E. Mann Foundation v. Cochlear Corp., No. 2:07-cv-08108-FMO-SH (C.D. Cal.).

Hugh McDermott, "An Advanced Cochlear Implant Hearing Prosthesis for Profound to Total Deafness," University of Melbourne Special Collections, June 1988, provided as Exhibit 1157 in Alfred E. Mann Foundation v. Cochlear Corp., No. 2:07-cv-08108-FMO-SH (C.D. Cal.).

Dr. Ir. S. Peeters et al., "The LAURA Cochlear Prosthesis: Development and Description," Cochlear Implant: Current Situation. Proceedings of the International Cochlear Symposium, Duren, West Germany, September 7-12, 1987, provided as Exhibit 1200 in Alfred E. Mann Foundation v. Cochlear Corp., No. 2:07-cv-08108-FMO-SH (C.D. Cal.).

Hugh McDermott, "A Custom LSI CMOS Chip for a Cochlear Implant," Journal of Electrical and Electronics Engineering, Australia-IE Aust. & IREE Aust., Vol. 4, No. 4, pp. 305-309, December 1984, provided as Exhibit 1197 in Alfred E. Mann Foundation v. Cochlear Corp., 2:07-cv-08108-FMO-SH (C.D. Cal.).

Hugh McDermott, "Cochlear Implant for Simultaneous Multichannel Stimulation," Annals of Otology, Rhinology & Laryngology, Vol. 96, No. 1, Part 2, Suppl. 128, pp. 67-69, Jan.-Feb. 1987, provided as Exhibit 1196 in Alfred E. Mann Foundation v. Cochlear Corp., No. 2:07-cv-08108-FMO-SH (C.D. Cal.).